United States Patent
Gonzalez et al.

(10) Patent No.: US 11,319,562 B2
(45) Date of Patent: May 3, 2022

(54) MODIFIED FATTY ACID BIOSYNTHESIS WITH ACP-DEPENDENT THIOLASES

(71) Applicants: Ramon Gonzalez, Tampa, FL (US); James M. Clomburg, Tampa, FL (US)

(72) Inventors: Ramon Gonzalez, Tampa, FL (US); James M. Clomburg, Tampa, FL (US)

(73) Assignee: Ramon Gonzalez, Tampa, FL (US)

( * ) Notice: Subject to any disclaimer, the term of this patent is extended or adjusted under 35 U.S.C. 154(b) by 0 days.

(21) Appl. No.: 16/815,790

(22) Filed: Mar. 11, 2020

(65) Prior Publication Data

US 2020/0277638 A1  Sep. 3, 2020

Related U.S. Application Data

(63) Continuation-in-part of application No. 15/566,705, filed as application No. PCT/US2016/027210 on Apr. 13, 2016, now abandoned.

(60) Provisional application No. 62/148,043, filed on Apr. 15, 2015.

(51) Int. Cl.
*C12N 9/00* (2006.01)
*C12P 7/6409* (2022.01)

(52) U.S. Cl.
CPC .................................. *C12P 7/6409* (2013.01)

(58) Field of Classification Search
CPC .................................... C12N 9/00; C12N 9/93
See application file for complete search history.

(56) References Cited

U.S. PATENT DOCUMENTS

2014/0273110 A1* 9/2014 Gonzalez .................. C12P 7/18
435/129

* cited by examiner

*Primary Examiner* — Tekchand Saidha
(74) *Attorney, Agent, or Firm* — Boulware & Valoir

(57) ABSTRACT

Methods of using microorganisms to make chemicals and fuels, including carboxylic acids, alcohols, hydrocarbons, and their alpha-, beta-, and omega-functionalized derivatives are described. Native or engineered thiolases are used condense a growing acyl-ACP and acetyl-ACP in combination with type II fatty acid synthesis. The resulting fatty acid biosynthesis cycle has an ATP yield analogous to the functional reverse β-oxidation cycle.

19 Claims, 22 Drawing Sheets

FIGURE 9A

A genetically engineered microorganism, said microorganism having means for performing a modified fatty acid biosynthesis (FAS) pathway that grows a primer by adding a 2-carbon donor thereto in each cycle, said modified FAS pathway comprising:
a) an overexpressed acetyl-CoA:ACP transacylase that catalyzes the conversion of acetyl-CoA to acetyl-ACP;
b) an overexpressed engineered ACP-dependent thiolase that catalyzes the non-decarboxylative condensation of an acyl-ACP primer with a 2-carbon donor acetyl-ACP or acetyl-CoA to produce a ß-ketoacyl-ACP;
c) an overexpressed 3-oxoacyl-[acyl-carrier-protein] reductase that catalyzes the reduction of a ß-ketoacyl-ACP to a ß-hydroxyacyl-ACP;
d) an overexpressed 3-hydroxyacyl-[acyl-carrier-protein] dehydratase that catalyzes the dehydration of a (3R)-ß-hydroxyacyl-ACP to a transenoyl-ACP;
e) an overexpressed enoyl-[acyl-carrier-protein] reductase that catalyzes the reduction of a transenoyl-ACP to an acyl-ACP that is two carbons longer than said acyl-ACP primer; and,
f) an overexpressed termination pathway that catalyzes the exit of an intermediate from said FAS cycle.

Preferably, the microorganism is bacteria or yeast or *E. coli* or other *Enterobacteriaceae*, preferably the overexpressed enzymes are under the control of an inducible promoter, and are either integrated or contained in an expression vector suitable for the host species.

A recombinant microorganism comprising an overexpressed ACP-dependent thiolase and one or more overexpressed Type II fatty acid synthesis enzymes, and an overexpressed termination enzyme, said microorganism able to run a modified fatty acid biosynthesis pathway with a non-decarboxylating condensation and produce a product using said termination enzyme to pull intermediates out of said modified fatty acid biosynthesis pathway.

A recombinant microorganism comprising an inducible expression vector or integrated sequence encoding an ACP-dependent thiolase and one or more overexpressed ACP-dependent thiolase and one or more overexpressed Type II fatty acid synthesis enzymes and an overexpressed termination enzyme, said microorganism able to run a modified fatty acid biosynthesis pathway with a non-decarboxylating condensation and produce a product using said termination enzyme to pull intermediates out of said modified fatty acid biosynthesis pathway.

A recombinant bacteria being an *E. coli* comprising an overexpressed ACP-dependent thiolase and one or more overexpressed Type II fatty acid synthesis enzymes and one or more overexpressed termination enzymes, said bacteria able to run a modified fatty acid biosynthesis pathway with a non-decarboxylating condensation and produce a product using said termination enzyme to pull intermediates out of said modified fatty acid biosynthesis pathway.

A recombinant bacteria being an *E. coli* comprising an inducible expression vector or integrated sequence encoding an ACP-dependent thiolase and one or more Type II fatty acid synthesis enzymes and one or more termination enzymes, said bacteria able to run a modified fatty acid biosynthesis pathway with a non-decarboxylating condensation and produce a product using said

FIGURE 9A CONTINUED

| |
|---|
| termination enzyme to pull intermediates out of said modified fatty acid biosynthesis pathway. |
| A recombinant microorganism comprising means for expressing an ACP-dependent thiolase, Type II fatty acid synthesis enzymes, and a termination enzyme, said microorganism able to run a modified fatty acid biosynthesis pathway with a non-decarboxylating condensation and produce a product using said termination enzyme to pull intermediates out of said modified fatty acid biosynthesis pathway. |
| A method of producing a product comprising growing a genetically engineered microorganism as described herein in a culture broth containing glycerol or a sugar, extending a ACP thioester primer by using said modified fatty acid biosynthesis pathway with a non-decarboxylative condensation to produce a product at least two carbons longer than said primer, and isolating said product. |
| Any microorganism herein described, wherein said termination pathway is an ACP cleaving thioesterase. |
| Any microorganism herein described, wherein said termination pathway produces a product selected from the group consisting of carboxylic acids, (3R)-β-hydroxy carboxylic acids, β-keto carboxylic acids, and α,β-unsaturated carboxylic acids. |
| Any microorganism herein described, wherein said termination pathway is selected from the group consisting i) an alcohol-forming ACP thioester reductase, and ii) an aldehyde-forming ACP thioester reductase and an alcohol dehydrogenase. |
| Any microorganism herein described, wherein said termination pathway produces a product selected from the group consisting of primary alcohols, 1,(3R)-β diols, β-keto primary alcohols, and α,β-unsaturated primary alcohols. |
| Any microorganism herein described, wherein said termination pathway consists of an aldehyde-forming ACP thioester reductase and aldehyde decarbonylase. |
| Any microorganism herein described, wherein said microorganism produces a product selected from the group consisting of linear alkanes, linear alkan-3-ols, linear methyl-ketones, and 1-alkenes. |
| Any microorganism herein described, wherein said termination pathway consists of an aldehyde-forming ACP thioester reductase and a transaminase. |
| Any microorganism herein described, wherein said microorganism produces a product selected from the group consisting of primary amines, 3-hydroxy-amines, 3-keto-amines, and α,β-unsaturated primary amines. |

FIGURE 9B

| |
|---|
| Any microorganism herein described, wherein said microorganism expresses a carboxylic acid omega hydroxylase and produces a product selected from the group consisting of ω-hydroxylated carboxylic acids, (3R)- β-, ω-dihydroxy carboxylic acids, β-keto, ω-hydroxy carboxylic acids, and α,β-unsaturated ω-hydroxylated carboxylic acids |
| Any microorganism herein described, wherein said microorganism expresses a carboxylic acid ω hydroxylase, an alcohol oxidase, and an aldehyde dehydrogenase, and produces a product selected from the group consisting of ω-hydroxylated carboxylic acids, (3R)-β-, ω-dihydroxy carboxylic acids, β-keto, ω-hydroxy carboxylic acids, and α,β-unsaturated omega-hydroxylated carboxylic acids |
| Any microorganism herein described, wherein said microorganism expresses a carboxylic acid ω hydroxylase, and produces a product selected from the group consisting of 1-,ω-diols, 1-,(3R)-β-, ω-triols, β-keto, 1-,ω-diols, and α,β-unsaturated 1-,ω-diols. |
| Any microorganism herein described, wherein said microorganism expresses a carboxylic acid ω hydroxylase, an alcohol oxidase, and an aldehyde dehydrogenase, and produces a product selected from the group consisting of di-carboxylic acids, (3R)-β-hydroxy di-carboxylic acids, β-keto di-carboxylic acids, and α,β-unsaturated di-carboxylic acids. |
| Any microorganism herein described, wherein said microorganism expresses a carboxylic acid ω hydroxylase, an alcohol oxidase, and a transaminase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines. |
| Any microorganism herein described, wherein said microorganism expresses a carboxylic acid ω hydroxylase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines. |
| Any microorganism herein described, wherein said microorganism expresses a carboxylic acid ω hydroxylase, an alcohol oxidase, and an aldehyde dehydrogenase, and produces a product selected from the group consisting of ω-amino acids, (3R)-β-hydroxy ω-amino acids, β-keto ω-amino acids, and α,β-unsaturated ω-amino acids. |
| Any microorganism herein described, wherein said microorganism expresses a carboxylic acid alpha hydroxylase, and produces a product selected from the group alpha-hydroxy carboxylic acids, alpha-,(3R)-β-dihydroxy carboxylic acids, α-hydroxy, β-keto carboxylic acids, and α,β-unsaturated α-hydroxy carboxylic acids. |
| Any microorganism herein described, wherein said microorganism expresses a carboxylic acid α hydroxylase, and produces a product selected from the group consisting of 1,2-diols, 1,2,3-triols, β-keto, 1,2-diols, and α,β-unsaturated 1,2-diols. |
| Any microorganism herein described, wherein said microorganism expresses a carboxylic acid α hydroxylase, and produces a product selected from the group consisting of α-hydroxylated primary amines, α-, β- dihydroxy primary amines, α-hydroxy, β-keto primary amines, and α-hydroxy, α,β-unsaturated primary amines. |

FIGURE 9B CONTINUED

| |
|---|
| Any microorganism herein described, further comprising reduced expression of fermentation enzymes leading to reduced production of lactate, acetate, ethanol and succinate. |
| Any microorganism herein described, wherein said overexpressed acetyl-CoA:ACP transacylase is encoded by E. coli fabD (P0AAI9), Streptomyces collinus fadA (Q93C88), or homologues. |
| Any microorganism herein described, wherein said overexpressed thiolase is a native or engineered variant of those encoded by E. coli atoB (NP_416728.1), E. coli yqeF (NP_417321.2), E. coli fadA (YP_026272.1), E. coli fadI (NP_416844.1), Streptomyces collinus fadA (Q93C88), Ralstonia eutropha bktB (AAC38322.1), Pseudomonas sp. Strain B13 catF (AAL02407.1), E. coli paaJ (NP_415915.1), Pseudomonas putida pcaF (AAA85138.1), Rhodococcus opacus pcaF (YP_002778248.1), Streptomyces sp. pcaF (AAD22035.1), Ralstonia eutropha phaA (AEI80291.1), Clostridium acetobutylicum thlA (AAC26023.1), or Clostridium acetobutylicum thlB (AAC26026.1), or homologues, able to catalyze the non-decarboxylative condensation of an acyl-ACP primer and acetyl-ACP extender unit. |
| Any microorganism herein described, wherein said overexpressed 3-oxoacyl-[acyl-carrier-protein] reductase is encoded by E. coli fabG (NP_415611.1), or homologues. |
| Any microorganism herein described, wherein said overexpressed 3-hydroxyacyl-[acyl-carrier-protein] dehydratase is encoded by E. coli fabA (NP_415474.1), E. coli fabZ (NP_414722.1), or homologues. |
| Any microorganism herein described, wherein said overexpressed enoyl-[acyl-carrier-protein] reductase is encoded by E. coli fabI (NP_415804.1), Enterococcus faecalis fabK (NP_816503.1), Bacillus subtilis fabL (KFK80655.1), Vibrio cholerae fabV (ABX38717.1), or homologues. |
| Any microorganism herein described, wherein said overexpressed ACP-cleaving thioesterase is encoded by E. coli tesA (NP_415027.1), Cuphea palustris fatB1 (AAC49179.1), Cuphea viscosissima fatB3 (AEM72524.1), Ulmus americana fatB1 (AAB71731.1), Cocos nucifera fatB2 (AEM72520.1), Elaeis guineensis PTE (AAD42220.2), Clostridium perfringens CPF_2954 (ABG82470.1), Umbellularia californica fatB1 (AAA34215.1), Bacteroides thetaiotaomicron bTE (AAO77182.1), Bacteroides fragilis tes4 (CAH09236.1), Marvinbryantia formatexigens BRYFOR_06758 (EET61113.1), or homologues. |
| Any microorganism herein described, wherein said overexpressed alcohol-forming ACP thioester reductase is encoded by Marinobacter aquaeolei VT8 maqu_2220 (YP_959486.1), Hahella chejuensis hch_05075 (ABC31758.1), Marinobacter algicola MDG893_11561 (A6EVI7), Bermanella marisrubri RED65_09894 (Q1N697), or homologues. |

FIGURE 9C

| |
|---|
| Any microorganism herein described, wherein said overexpressed aldehyde-forming ACP thioester reductase is encoded by *Nostoc punctiforme* Npun_R1710 (ACC80381.1), *Synechococcus elongates* Synpcc7942_1594 (Q54765), *Prochlorococcus marinus* P9515_05971 (A2BVJ5), *Synechocystis* sp. PCC 6803 sll0209 (YP_005652204.1), or homologues. |
| Any microorganism herein described, wherein said overexpressed alcohol dehydrogenase is encoded by *E. coli betA* (NP_414845.1), *E. coli dkgA* (NP_417485.4), *E. coli eutG* (NP_416948.4), *E. coli fucO* (NP_417279.2), *E. coli ucpA* (NP_416921.4), *E. coli yahK* (NP_414859.1), *E. coli ybbO* (NP_415026.1), *E. coli ybdH* (NP_415132.1), *E. coli yiaY* (YP_026233.1), *E. coli yjgB* (NP_418690.4), homologues. |
| Any microorganism herein described, wherein said aldehyde decarbonylase overexpressed is encoded by *Synechococcus elongatus* PCC7942 orf1593 (Q54764.1), *Nostoc punctiforme* PCC73102 npun_R1711 (B2J1M1.1), *Prochlorococcus marinus* MIT9313 pmt1231 (Q7V6D4.1), or homologues. |
| Any microorganism herein described, wherein said overexpressed transaminase is encoded by *Arabidopsis thaliana* At3g22200 (NP_001189947.1), *Alcaligenes denitrificans* aptA (AAP92672.1), *Bordetella bronchiseptica* BB0869 (WP_015041039.1), *Bordetella parapertussis* BPP0784 (WP_010927683.1), *Brucella melitensis* BAWG_0478 (EEW88370.1), *Burkholderia pseudomallei* BP1026B_I0669 (AFI65333.1), *Chromobacterium violaceum* CV2025 (AAQ59697.1), *Oceanicola granulosus* OG2516_07293 (WP_007254984.1), *Paracoccus denitrificans* PD1222 Pden_3984 (ABL72050.1), *Pseudogulbenkiania ferrooxidans* ω-TA (WP_008952788.1), *Pseudomonas putida* ω-TA (P28269.1), *Ralstonia solanacearum* ω-TA (YP_002258353.1), *Rhizobium meliloti* SMc01534 (NP_386510.1), and *Vibrio fluvialis* ω-TA (AEA39183.1), *Mus musculus abaT* (AAH58521.1) *E. coli gabT* (YP_490877.1), or homologues. |
| Any microorganism herein described, wherein said overexpressed carboxylic acid omega hydroxylase is encoded by *Pseudomonas putida* alkBGT (YP_009076004.1, Q9WWW4.1, Q9L4M8.1),*Marinobacter aquaeolei* CYP153A (ABM17701.1), *Mycobacterium marinum* CYP153A16 (YP_001851443.1), *Polaromonas* sp. CYP153A (YP_548418.1), *Nicotiana tabacum* CYP94A5 (AAL54887.1), *Vicia sativa* CYP94A1 (AAD10204.1), *Vicia sativa* CYP94A2 (AAG33645.1), *Arabidopsis thaliana* CYP94B1 (BAB08810.1), *Arabidopsis thaliana* CYP86A8 (CAC67445.1), *Candida tropicalis* CYP52A1 (AAA63568.1, AAA34354.1, AAA34334.1), *Candida tropicalis* CYP52A2 (AAA34353.2, CAA35593.1), *Homo sapiens* CYP4A11 (AAQ56847.1), or homologues. |
| Any microorganism herein described, wherein said overexpressed alcohol oxidase is encoded by *Rhodococcus ruber* SC1 *cddC* (AAL14237.1), *Acinetobacter* sp. SE19 *chnD* (AAG10028.1), *E. coli yahK* (NP_414859.1), *E. coli yjgB* (NP_418690.4), or homologues. |
| Any microorganism herein described, wherein said overexpressed aldehyde dehydrogenase is encoded by *Rhodococcus ruber* SC1 *cddD* (AAL14238.1), *Acinetobacter* sp. SE19 *chnE* (AAG10022.1), or homologues. |
| Any microorganism herein described, wherein said overexpressed fatty acid alpha hydroxylases is encoded by *Myxococcus* |

FIGURE 9C CONTINUED

| |
|---|
| xanthus MXAN_0191 (YP_628473.1), Stigmatella aurantiaca STIAU_3334 (YP_003957653.1), or homologues. |
| Any microorganism herein described, wherein said overexpressed thiolase is an engineered variant of those encoded by E. coli atoB (NP_416728.1), E. coli yqeF (NP_417321.2), E. coli fadA (YP_026272.1), E. coli fadI (NP_416844.1), Streptomyces collinus fadA (Q93C88), Ralstonia eutropha bktB (AAC38322.1), Pseudomonas sp. Strain B13 catF (AAL02407.1), E coli paaJ (NP_415915.1), Pseudomonas putida pcaF (AAA85138.1), Rhodococcus opacus pcaF (YP_002778248.1), Streptomyces sp. pcaF (AAD22035.1), Ralstonia eutropha phaA (AEI80291.1), Clostridium acetobutylicum thlA (AAC26023.1), or Clostridium acetobutylicum thlB (AAC26026.1), or homologues, able to catalyze the non-decarboxylative condensation of an omega-hydroxylated primer, an omega-carboxylated primer, an omega-phenyl-terminated primer, an omega-aminated primer, or an aliphatic branched primer with acetyl-ACP. |
| Any microorganism herein described, wherein said overexpressed 3-oxoacyl-[acyl-carrier-protein] reductase, overexpressed 3-hydroxyacyl-[acyl-carrier-protein] dehydratase, and overexpressed enoyl-[acyl-carrier-protein] reductase are able to act on omega-hydroxylated, omega-carboxylated, omega-phenyl-terminated, omega-aminated, or aliphatic branched substrates and encoded by genes selected from the group consisting of E. coli fabG (NP_415611.1), E. coli fabA (NP_415474.1), E. coli fabZ (NP_414722.1), E. coli fabI (NP_415804.1), Enterococcus faecalis fabK (NP_816503.1), Bacillus subtilis fabL (KFK80655.1), Vibrio cholerae fabV (ABX38717.1), or homologues. |

FIGURE 9D

| |
|---|
| Any microorganism herein described, wherein said overexpressed termination pathways are able to act on omega-hydroxylated, omega-carboxylated or omega-aminated substrates and encoded by genes selected from the group consisting of *E. coli tesA* (NP_415027.1), *Cuphea palustris fatB1* (AAC49179.1), *Cuphea viscosissima fatB3* (AEM72524.1), *Ulmus americana fatB1* (AAB71731.1), *Cocos nucifera fatB2* (AEM72520.1), *Elaeis guineensis PTE* (AAD42220.2), *Clostridium perfringens CPF_2954* (ABG82470.1), *Umbellularia californica fatB1* (AAA34215.1), *Marinobacter aquaeolei VT8 maqu_2220* (YP_959486.1), *Hahella chejuensis hch_05075* (ABC31758.1), *Marinobacter algicola MDG893_11561* (A6EVI7), *Bermanella marisrubri RED65_09894* (Q1N697), *Nostoc punctiforme Npun_R1710* (ACC80381.1), *Synechococcus elongates Synpcc7942_1594* (Q54765), *Prochlorococcus marinus P9515_05971* (A2BVJ5), *Synechocystis sp. PCC 6803 sll0209* (YP_005652204.1), *E. coli betA* (NP_414845.1), *E. coli dkgA* (NP_417485.4), *E. coli eutG* (NP_416948.4), *E. coli fucO* (NP_417279.2), *E. coli ucpA* (NP_416921.4), *E. coli yahK* (NP_414859.1), *E. coli ybbO* (NP_415026.1), *E. coli ybdH* (NP_415132.1), *E. coli yiaY* (YP_026233.1), *E. coli yjgB* (NP_418690.4), *Synechococcus elongatus PCC7942 orf1593* (Q54764.1), *Nostoc punctiforme PCC73102 npun_R1711* (B2J1M1.1), *Prochlorococcus marinus MIT9313 pmt1231* (Q7V6D4.1), *Arabidopsis thaliana At3g22200* (NP_001189947.1), *Alcaligenes denitrificans aptA* (AAP92672.1), *Bordetella bronchiseptica BB0869* (WP_015041039.1), *Bordetella parapertussis BPP0784* (WP_010927683.1), *Bordetella melitensis BAWG_0478* (EEW88370.1), *Burkholderia pseudomallei BP1026B_I0669* (AFI65333.1), *Chromobacterium violaceum CV2025* (AAQ59697.1), *Oceanicola granulosus OG2516_07293* (WP_007254984.1), *Paracoccus denitrificans PD1222 Pden_3984* (ABL72050.1), *Pseudogulbenkiania ferrooxidans ω-TA* (WP_008952788.1), *Pseudomonas putida ω-TA* (P28269.1), *Ralstonia solanacearum ω-TA* (YP_002258353.1), *Rhizobium melliloti SMc01534* (NP_386510.1), and *Vibrio fluvialis ω-TA* (AEA39183.1), *Mus musculus abaT* (AAH58521.1) *E. coli gabT* (YP_490877.1), or homologues. |
| Any microorganism herein described, wherein said reduced expression of fermentation enzymes are ΔadhE, (Δpta or ΔackA or ΔackApta), ΔpoxB, ΔldhA, and ΔfrdA and less acetate, lactate, ethanol and succinate are thereby produced. |
| Any microorganism herein described, comprising one or more termination enzymes from Tables C and D. |

MODIFIED FATTY ACID BIOSYNTHESIS WITH ACP-DEPENDENT THIOLASES

PRIOR RELATED APPLICATIONS

This application is a continuation-in-part of U.S. Ser. No. 15/566,705 which is a National Phase under 35 U.S.C. § 371 of International Application PCT/US2016/27210, filed Apr. 13, 2016, which claims priority to U.S. App. No. 62/148,043, MODIFIED FATTY ACID BIOSYNTHESIS WITH ACP-DEPENDENT THIOLASES, filed Apr. 15, 2015. All applications are expressly incorporated by reference herein in their entirety for all purposes.

FEDERALLY SPONSORED RESEARCH STATEMENT

This invention was made with government support under Grant Nos: CBET1067565 and CBET1134541 awarded by the National Science Foundation. The government has certain rights in the invention.

FIELD OF THE DISCLOSURE

The disclosure generally relates to the use of microorganisms to make chemicals and fuels (e.g. carboxylic acids, alcohols, hydrocarbons, and their alpha-, beta-, and omega-functionalized derivatives), by utilizing a modified fatty acid biosynthesis (FAS) pathway with native or engineered thiolases capable of the non-decarboxylative condensation of acyl-ACP primers with acetyl-ACP extender units.

BACKGROUND OF THE DISCLOSURE

To date, the fatty acid biosynthesis pathway has been widely used as the means to generate higher-chain (C≥4) acyl-CoA thioesters required for the synthesis of the aforementioned products. The wild type pathway utilizes decarboxylative Claisen condensation reactions with malonyl thioesters as extender units and hence its operation is less efficient because ATP is consumed in the synthesis of malonyl-ACP, which is the donor of two-carbon units for chain elongation. As a consequence, the ATP yield associated with the production of products such as hydrocarbons through the fatty acid synthesis pathway is very low. This, in turn, greatly limits cell growth and product synthesis.

In order to overcome this limitation, we have recently implemented a novel approach by driving beta oxidation in reverse to make fatty acids instead of degrading them (see US20130316413, WO2013036812, each incorporated by reference in its entirety for all purposes). Unlike the fatty acid biosynthesis pathway, the reversal of the β-oxidation cycle operates with coenzyme-A (CoA) thioester intermediates and uses acetyl-CoA directly for acyl-chain elongation (rather than first requiring ATP-dependent activation to malonyl-CoA).

This disclosure takes the next step and illustrates an alternative approach to overcoming the ATP yield through the use of a native or engineered thiolase capable of performing a non-decarboxylative condensation between a growing acyl-(acyl-carrier-protein) (acyl-ACP) and acetyl-ACP to form a β-ketoacyl-ACP 2 carbons longer than the starting acyl-ACP. This reaction enables the circumvention of the energy intensive steps of the fatty acid biosynthesis pathway (formation of malonyl-ACP from acetyl-CoA), thus allowing the production of products via the fatty acid biosynthesis pathway analogous to a beta-oxidation reversal in terms of ATP yield.

An engineered microorganism having this modified fatty acid biosynthesis cycle that produces alcohols, carboxylic acids, and hydrocarbons, and derivatives thereof, generally includes: i) expression of native or engineered thiolases capable of performing a non-decarboxylative condensation between a growing acyl-ACP and acetyl-ACP, ii) functional operation of the remaining fatty acid biosynthesis steps for the reduction, dehydration, and second reduction of the β-ketoacyl-ACP formed the previous step, and iii) overexpression of one or more termination enzymes that convert ACP intermediates to a desired alcohol, carboxylic acid, or hydrocarbon, thus exiting or terminating the cycle for that intermediate. Further, any of the alcohols, carboxylic acids, and hydrocarbon products can be further modified to make other products in secondary termination pathways.

SUMMARY OF THE DISCLOSURE

This disclosure demonstrates that native or engineered thiolases capable of performing a non-decarboxylative condensation between a growing acyl-ACP and acetyl-ACP can be used in combination with enzymes from the type II (a discrete set of enzymes) fatty acid synthesis ("FAS") to operate a fatty acid biosynthesis cycle with an ATP yield analogous to a functional reversal of the β-oxidation cycle.

Key to achieving this more ATP efficient fatty acid biosynthesis cycle is a thiolase, a class of enzymes whose native substrate(s) are CoA intermediates, capable of condensing an acyl-ACP and acetyl-ACP in a non-decarboxylative fashion parallel to their native function with CoA intermediates. As such, the use of a native or engineered thiolase capable of performing this non-decarboxylative condensation with ACP substrates will avoid the use of malonyl-ACP during the traditional decarboxylative condensation employed during FAS elongation, and as a result remove the ATP consumption mandated by the requirement of malonyl-ACP synthesis from acetyl-CoA. Thus, by employing this ACP-dependent thiolase for the condensation of the initial acyl-ACP primer, as well as chain elongation of the growing acyl-ACP, with acetyl-ACP the energy intensive steps consuming ATP during the fatty acid biosynthesis pathway can be circumvented.

Specifically, a combination of such a thiolase(s) with a 3-oxoacyl-[acyl-carrier-protein] reductase (FabG, others), 3-hydroxyacyl-[acyl-carrier-protein] dehydratase (FabA, FabZ, others), and enoyl-[acyl-carrier-protein] reductase (FabI, FabK, FabL, FabV, others) yields a fatty acid biosynthesis cycle which does not require the energy intensive step involved in the synthesis of malonyl-ACP, the typical carbon donor in FAS elongation. Once this cycle is coupled with the appropriate priming and termination pathways, the production of carboxylic acids, alcohols, hydrocarbons, amines and their α-, β-, and ω-functionalized derivatives from numerous carbon sources can be achieved.

As used herein, a "primer" is a starting molecule for the FAS cycle to add two carbon donor units to. The initial primer is either typically acetyl-ACP or propionyl-ACP, but as the chain grows by adding donor units in each cycle, the primer will accordingly increase in size. In some cases, the bacteria can also be provided with larger primers, e.g., C4 primers, etc. added to the media or obtained from other cell pathways. Further, non-traditional primers can be used wherever atypical products are desired (i.e., hydroxylated primers, carboxylated primers, etc. . . . ).

As used herein, the "donor" of the 2 carbon units is acetyl-ACP.

As used herein "type II fatty acid synthesis enzymes" refer to those enzymes that function independently, e.g., are discrete, monofunctional enzymes, used in fatty acid synthesis. Type II enzymes are found in archaea and bacteria. Type I systems, in contrast, utilize a single large, multifunctional polypeptide.

"Thiolases" are ubiquitous enzymes that have key roles in many vital biochemical pathways, including the beta oxidation pathway of fatty acid degradation and various biosynthetic pathways. Members of the thiolase family can be divided into two broad categories: degradative thiolases (EC 2.3.1.16), and biosynthetic thiolases (EC 2.3.1.9). The forward and reverse reactions are shown below:

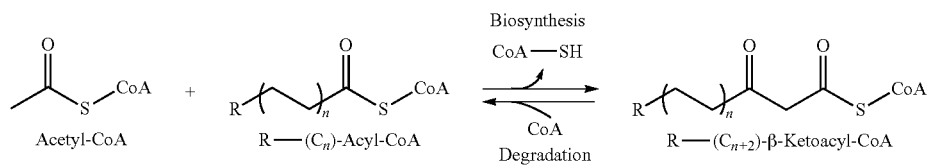

These two different types of thiolase are found both in eukaryotes and in prokaryotes: acetoacetyl-CoA thiolase (EC:2.3.1.9) and 3-ketoacyl-CoA thiolase (EC:2.3.1.16). 3-ketoacyl-CoA thiolase (also called thiolase I) has a broad chain-length specificity for its substrates and is involved in degradative pathways such as fatty acid beta-oxidation. Acetoacetyl-CoA thiolase (also called thiolase II) is specific for the thiolysis of acetoacetyl-CoA and involved in biosynthetic pathways such as poly beta-hydroxybutyric acid synthesis or steroid biogenesis.

Furthermore, the thiolases can be made to run in the reverse direction by building up the level of left hand side reactants (primer and extender unit), thus driving the equilibrium in the forward direction. We have previously demonstrated that this approach can be used to operate thiolases in the biosynthetic direction, enabling the synthesis of various chain length products through a reversal of the beta-oxidation cycle operating with CoA intermediates (see US20130316413, WO2013036812, each incorporated by reference in its entirety for all purposes). Here, we further exploit the ability of thiolases to function in the synthetic direction by demonstrating these enzymes can function with ACP intermediates (e.g. acetyl-ACP or acyl-ACP), key to the operation of a more energy (ATP) efficient fatty acid biosynthesis pathway.

Many examples of thiolase enzymes which can potentially catalyze the non-decarboxylative condensation of an acyl-ACP primer and acetyl-ACP extender unit are provided herein and the following Table A provides several additional examples which can also serve as templates for engineered variants:

TABLE A

| Example Thiolase Enzymes (EC Number 2.3.1.-) | |
|---|---|
| Source organism and gene name | Protein Accession Numbers |
| E. coli atoB | NP_416728.1 |
| E. coli yqeF | NP_417321.2 |
| E. coli fadA | YP_026272.1 |
| E. coli fadI | NP_416844.1 |
| Streptomyces collinus fadA | Q93C88 |

TABLE A-continued

| Example Thiolase Enzymes (EC Number 2.3.1.-) | |
|---|---|
| Source organism and gene name | Protein Accession Numbers |
| Ralstonia eutropha bktB | AAC38322.1 |
| Pseudomonas sp. Strain B13 catF | AAL02407.1 |
| E coli paaJ | NP_415915.1 |
| Pseudomonas putida pcaF | AAA85138.1 |
| Rhodococcus opacus pcaF | YP_002778248.1 |
| Streptomyces sp. pcaF | AAD22035.1 |
| Ralstonia eutropha phaA | AEI80291.1 |
| Clostridium acetobutylicum thlA | AAC26023.1 |
| Clostridium acetobutylicum thlB | AAC26026.1 |

As used herein, an "ACP-dependent thiolase" is an enzyme that catalyzes the condensation of an acyl-ACP or other primer with a 2-carbon donor acetyl-ACP to produce a ß-ketoacyl-ACP in a non-decarboxylative condensation reaction.

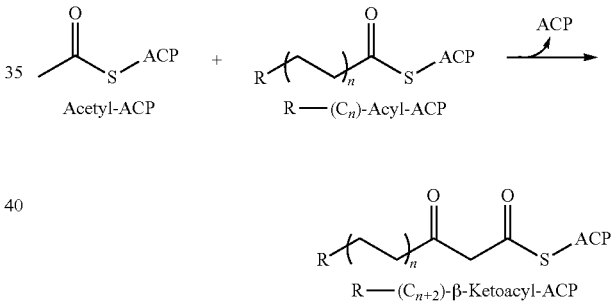

As used herein a "3-oxoacyl-[acyl-carrier-protein] reductase" or "3-oxoacyl-[ACP] reductase" is an enzyme that catalyzes the reduction of a ß-ketoacyl-ACP to a (3R)-ß-hydroxyacyl-ACP:

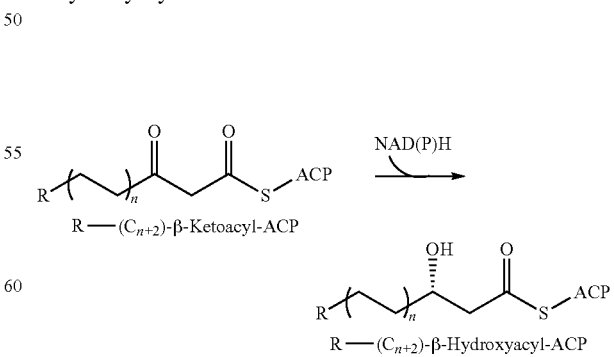

As used herein, a "3-hydroxyacyl-[ACP] dehydratase" is an enzyme that catalyzes the dehydration of a (3R)-ß-hydroxyacyl-ACP to a transenoyl-ACP:

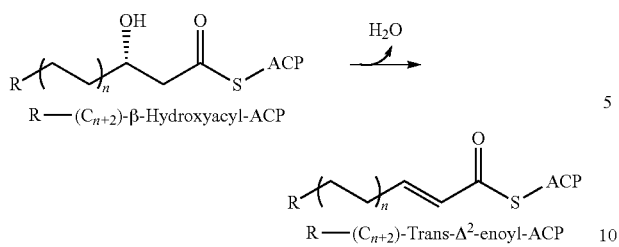

R—($C_{n+2}$)-β-Hydroxyacyl-ACP

R—($C_{n+2}$)-Trans-$\Delta^2$-enoyl-ACP

As used herein, an "enoyl-[ACP] reductase" that catalyzes the reduction of a transenoyl-ACP to an acyl-ACP:

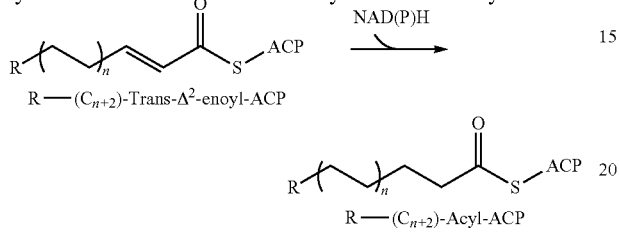

R—($C_{n+2}$)-Trans-$\Delta^2$-enoyl-ACP

R—($C_{n+2}$)-Acyl-ACP

The needed FAS enzymes are found in all type II FAS organisms, and thus there are hundreds (if not thousands) available to choose from. Examples of FAS enzymes catalyzing these reactions are provided herein and the following Table B provides several additional examples:

TABLE B

Example FAS Enzymes for Cycle Reaction Steps (See above for reaction illustrations)

| Reaction | Source organism and gene name | Protein Accession Numbers |
| --- | --- | --- |
| β-ketoacyl-ACP → (3R)-β-hydroxyacyl-ACP | E. coli fabG | NP_415611.1 |
| (3R)-β-hydroxyacyl-ACP → transenoyl-ACP | E. coli fabA | NP_415474.1 |
|  | E. coli fabZ | NP_414722.1 |
| transenoyl-ACP → acyl-ACP | E. coli fabI | NP_415804.1 |
|  | Enterococcus faecalis fabK | NP_816503.1 |
|  | Bacillus subtilis fabL | KFK80655.1 |
|  | Vibrio cholerae fabV | ABX38717.1 |

Combination of ACP-dependent thiolases and the remaining steps of the fatty acid biosynthesis pathway (such as FabG, FabZ, and FabI) provide an energy efficient route for the generation of various chain length ACP intermediates, which can be converted to numerous valuable fuels and chemicals (FIG. 1).

As used herein "termination pathway" refers to one or more enzymes (or genes encoding same) that will pull reaction intermediates out the FAS cycle and produce the desired end product.

By "primary termination pathway" what is meant is an intermediate from the FAS cycle is pulled out of the FAS cycle by one (which can have more than one activity) or more termination enzymes and results in i) carboxylic acids, ii) primary alcohols, iii) hydrocarbons, or iv) primary amines, from ACP intermediates as described in FIG. 1.

By "secondary termination pathway" what is meant is that the intermediate pulled out of the FAS cycle by a primary termination pathway enzyme is further modified by one or more enzymes.

Many examples of termination pathways are provided herein and the following Table C provides several examples:

TABLE C

Termination Pathways for Conversion of ACP Intermediates to Desired Products

| Reaction | Illustration | EC Numbers | Enzyme names | Source organism and gene name | Protein Accession Numbers |
| --- | --- | --- | --- | --- | --- |
| Acyl-ACP → Carboxylic acid | Acyl-ACP → Carboxylic Acid | 3.1.2.- | Thioesterase | E. coli tesA | NP_415027.1 |
|  |  |  |  | Cuphea palustris fatB1 | AAC49179.1 |
|  |  |  |  | Cuphea viscosissima fatB3 | AEM72524.1 |

TABLE C-continued

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| | | | | *Ulmus americana* fatB1 | AAB71731.1 |
| | | | | *Cocos nucifera* fatB2 | AEM72520.1 |
| | | | | *Elaeis guineensis* PTE | AAD42220.2 |
| | | | | *Clostridium perfringens* CPF_2954 | ABG82470.1 |
| | | | | *Umbellularia californica* fatB1 | AAA34215.1 |
| | | | | *Bacteroides thetaiotaomicron* bTE | AAO77182.1 |
| | | | | *Bacteroides fragilis* tes4 | CAH09236.1 |
| | | | | *Marvinbryantia formatexigens* BRYFOR_06758 | EET61113.1 |
| Acyl-ACP → Alcohol | Acyl-ACP → Primary Alcohol | 1.2.1.- | Alcohol-forming ACP reductase | *Marinobacter aquaeolei* VT8 maqu_2220 | YP_959486.1 |
| | | | | *Hahella chejuensis* hch_05075 | ABC31758.1 |
| | | | | *Marinobacter algicola* MDG893_11561 | A6EVI7 |
| | | | | *Bermanella marisrubri* RED65_09894 | Q1N697 |
| Acyl-ACP → Aldehyde | Acyl-ACP → Aldehyde | 1.2.1.80 | Aldehyde forming ACP reductase | *Nostoc punctiforme* Npun_R1710 | ACC80381.1 |
| | | | | *Synechococcus elongates* Synpcc7942_1594 | Q54765 |
| | | | | *Prochlorococcus marinus* P9515_05971 | A2BVJ5 |
| | | | | *Synechocystis* sp. PCC 6803 sll0209 | YP_005652204.1 |
| Aldehyde → Alcohol | An aldehyde → An alcohol | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| Aldehyde → Alkane | An aldehyde → An alkane | 4.1.99.5 | Aldehyde decarbonylase | *Synechococcus elongates* PCC7942 orf1593 | Q54764.1 |
| | | | | *Nostoc punctiforme* PCC73102 npun_R1711 | B2J1M1.1 |
| | | | | *Prochlorococcus marinus* MIT9313 pmt1231 | Q7V6D4.1 |
| Aldehyde → Amine | An aldehyde → An amine | 2.6.1.- | Transaminase | *Arabidopsis thaliana* At3g22200 | NP_001189947.1 |
| | | | | *Alcaligenes denitrificans* AptA | AAP92672.1 |
| | | | | *Bordetella bronchiseptica* BB0869 | WP_015041039.1 |
| | | | | *Bordetella parapertussis* BPP0784 | WP_010927683.1 |

TABLE C-continued

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| | | | | *Brucella melitensis* BAWG_0478 | EEW88370.1 |
| | | | | *Burkholderia pseudomallei* BP1026B_I0669 | AFI65333.1 |
| | | | | *Chromobacterium violaceum* CV2025 | AAQ59697.1 |
| | | | | *Oceanicola granulosus* OG2516_07293 | WP_007254984.1 |
| | | | | *Paracoccus denitrificans* PD1222 Pden_3984 | ABL72050.1 |
| | | | | *Pseudogulbenkiania ferrooxidans* ω-TA | WP_008952788.1 |
| | | | | *Pseudomonas putida* ω-TA | P28269.1 |
| | | | | *Ralstonia solanacearum* ω-TA | YP_002258353.1 |
| | | | | *Rhizobium meliloti* SMc01534 | NP_386510.1 |
| | | | | *Vibrio fluvialis* ω-TA | AEA39183.1 |
| | | | | *Mus musculus* abaT | AAH58521.1 |
| | | | | *E. coli* gabT | YP_490877.1 |
| Carboxylic Acid → ω-hydroxyacid | 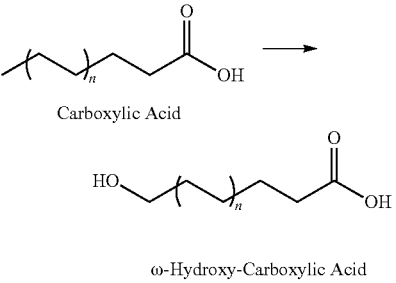 | 1.14.- | Carboxylic acid omega hydroxylase | *Pseudomonas putida* alkBGT | YP_009076004.1, Q9WWW4.1, Q9L4M8.1 |
| | | | | *Marinobacter aquaeolei* CYP153A | ABM17701.1 |
| | | | | *Mycobacterium marinum* CYP153A16 | YP_001851443.1 |
| | | | | *Polaromonas* sp. CYP153A | YP_548418.1 |
| | | | | *Nicotiana tabacum* CYP94A5 | AAL54887.1 |
| | | | | *Vicia sativa* CYP94A1 | AAD10204.1 |
| | | | | *Vicia sativa* CYP94A2 | AAG33645.1 |
| | | | | *Arabidopsis thaliana* CYP94B1 | BAB08810.1 |
| | | | | *Arabidopsis thaliana* CYP86A8 | CAC67445.1 |
| | | | | *Candida tropicalis* CYP52A1 | AAA63568.1, AAA34354.1, AAA34334.1 |
| | | | | *Candida tropicalis* CYP52A2 | AAA34353.2, CAA35593.1 |
| | | | | *Homo sapiens* CYP4A11 | AAQ56847.1 |
| ω-hydroxyacid → ω-oxo-acid | 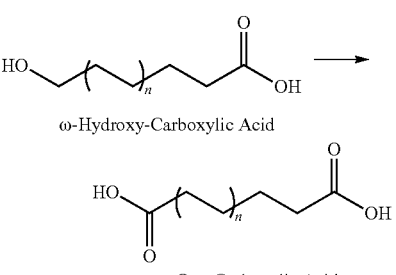 | 1.1.1.- | Alcohol oxidase/alcohol dehydrogenase | *Rhodococcus ruber* SC1 cddC | AAL14237.1 |
| | | | | *Acinetobacter* sp. SE19 chnD | AAG10028.1 |
| | | | | *E. coli* yahK | NP_414859.1 |
| | | | | *E. coli* yjgB | NP_418690.4 |

TABLE C-continued

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| ω-oxo acid → dicarboxylic acid | ω-Oxo-Carboxylic Acid → Dicarboxylic Acid | 1.2.1.- | Aldehyde dehydrogenase | Rhodococcus ruber SC1 cddD | AAL14238.1 |
|  |  |  |  | Acinetobacter sp. SE19 chnE | AAG10022.1 |
| Carboxylic Acid → α-hydroxyacid | A carboxylic acid → An alpha hydroxy-carboxylic acid | 1.14.- | Carboxylic acid alpha hydroxylase | Myxococcus xanthus MXAN_0191 | YP_628473.1 |
|  |  |  |  | Stigmatella aurantiaca STIAU_3334 | YP_003957653.1 |

Many microbes do not make significant amounts of free fatty acids, but can be made to do so by adding a gene coding for an Acyl-acyl carrier protein (ACP) thioesterase (called a "TE" gene herein). Acyl-ACP thioesterase is an enzyme that terminates the intraplastidial fatty acid synthesis by hydrolyzing the acyl-ACP intermediates and releasing free fatty acids to be incorporated into glycerolipids. These enzymes are classified in two families, FatA and FatB, which differ in amino acid sequence and substrate specificity. Generally speaking, the N terminal (aa 1-98) of any acyl-ACP thioesterase controls the substrate specificity of the enzyme, and it is known how to change substrate specificity by swapping amino terminal domains.

Many acyl-ACP thioesterase proteins are known and can be added to bacteria for use in the invention (e.g., CAA52070, YP_003274948, ACY23055, AAB71729, BAB33929, to name a few of the thousands of such proteins available). Such genes can be added by plasmid or other vector, or can be cloned directly into the genome. In certain species it may also be possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity, although permanent modifications to the genome may be preferred in the long term for stability reasons.

Other fatty acyl ACP thioesterases include Umbellularia californica (GenBank #AAC49001), Cinnamomum camphora (GenBank #Q39473), Umbellularia californica (GenBank #Q41635), Myristica fragrans (GenBank #AAB71729), Myristica fragrans (GenBank #AAB71730), Elaeis guineensis (GenBank #ABD83939), Elaeis guineensis (GenBank #AAD42220), Populus tomentosa (GenBank #ABC47311), Arabidopsis thaliana (GenBank #NP-172327), Arabidopsis thaliana (GenBank #CAA85387), Arabidopsis thaliana (GenBank #CAA85388), Gossypium hirsutum (GenBank #Q9SQI3), Cuphea lanceolata (GenBank #CAA54060), Cuphea hookeriana (GenBank #AAC72882), Cuphea calophylla subsp. mesostemon (GenBank #ABB71581), Cuphea lanceolata (GenBank #CAC19933), Elaeis guineensis (GenBank #AAL15645), Cuphea hookeriana (GenBank #Q39513), Gossypium hirsutum (GenBank #AAD01982), Vitis vinifera (GenBank #CAN81819), Garcinia mangostana (GenBank #AAB51525), Brassica juncea (GenBank #ABI18986), Madhuca longifolia (GenB ank #AAX51637), Brassica napus (GenBank #ABH11710), Oryza sativa (indica cultivar-group) (GenBank #EAY86877), Oryza sativa (japonica cultivar-group) (GenBank #NP-001068400), Oryza sativa (indica cultivar-group) (GenBank #EAY99617), and Cuphea hookeriana (GenBank #AAC49269). Other TEs include the TesA or TesB from E. coli or YJR019C, YTE1 or YTE2 from yeast or the TE from humans or other mammals.

In some embodiments, at least one TE gene is from a plant, for example overexpressed acyl-ACP thioesterase gene from Ricinus communis, Jatropha curcas, Diploknema butyracea, Cuphea palustris, or Gossypium hirsutum, or an overexpressed hybrid acyl-ACP thioesterase comprising different thioesterase domains operably fused together (see WO2011116279, incorporated by reference herein in its entirety for all purposes). Preferably, the hybrid thioesterase includes a terminal region of the acyl-ACP thioesterase from Ricinus communis or a 70, 80, 90 or 95% homolog thereto operably coupled to the remaining portion of the thioesterase from another species. In such manner, enzyme specificity can be tailored for the use in question.

In particular, the microorganism can comprise an overexpressed hybrid acyl-ACP thioesterase comprising the amino terminal region of the thioesterase from Ricinus communis operably coupled to the carboxyl region of the thioesterase from another species. Such microorganisms can be combined with each of the other mutations and overexpressions described herein in any combination.

It is also known to change the chain length of the FFAs by changing the TE: 1) Class I acyl-ACP TEs act primarily on 14- and 16-carbon acyl-ACP substrates; 2) Class II acyl-ACP TEs have broad substrate specificities, with major activities toward 8- and 14-carbon acyl-ACP substrates; and 3) Class III acyl-ACP TEs act predominantly on 8-carbon acyl-ACPs.

For example, most thioesterases exhibit the highest specificities in the C16-C18 range, including *A. thaliana* FatA (18:1Δ9), *Madhuca longifolia* FatB (16:0, 16:1, 18:0, 18:1), *Coriandrum sativum* FatA (18:1Δ9), *A. thaliana* FatB (16:0, 18:1, 18:0, 16:1), *Helianthus annuus* FatA (18:1, 16:1), and *Brassica juncea* FatB2 (16:0, 18:0), among numerous others. Medium-chain acyl-ACP thioesterases include *Cuphea palustris* FatB1 and *C. hookeriana* FatB2 (8:0, 10:0), *C. palustris* FatB2 (14:0, 16:0); and *Umbellularia californica* FatB (12:0, 12:1, 14:0, 14:1). Arecaceae (palm family) and *Cuphea* accumulate large quantities of fatty acids that are shorter (between 8 and 12 carbon atoms), and several enzymes are also available in bacteria. Exemplary thioesterase families and common names of their members are shown in Table D:

TABLE D

Thioesterase Families and Common Names of their Members

| Family | Producing organisms | Genes and/or other names of family members |
|---|---|---|
| TE1 | A, B, E[a] | Ach1 |
| TE2 | A, B, E | Acot1-Acot6, BAAT thioesterase |
| TE3 | A, B | tesA, acyl-CoA thioesterase I, protease I, lysophospholipase L1 |
| TE4 | B, E | tesB, acyl-CoA thioesterase II, Acot8 |
| TE5 | B | tesC (ybaW), acyl-CoA thioesterase III |
| TE6 | A, B, E | Acot7 (BACH), Acot11 (BFIT, Them1), Acot12 (CACH), YciA |
| TE7 | B, E | Acot9, Acot10 |
| TE8 | A, B, E | Acot13 (Them2) |
| TE9 | B | YbgC |
| TE10 | B | 4HBT-I |
| TE11 | B | 4HBT-II, EntH (YbdB) |
| TE12 | B, E | DNHA-CoA hydrolase |
| TE13 | A, B | paaI, paaD |
| TE14 | B, E | FatA, FatB |
| TE15 | B | Thioesterase CalE7 |
| TE16 | A, B, E | TE domain of FAS (Thioesterase I), TE domain of PKS or NRP (type I thioesterase (TE I)) |
| TE17 | B | TE domain of PKS |
| TE18 | B, E | Thioesterase II, type II thioesterase (TE II) |
| TE19 | B | luxD |
| TE20 | E | ppt1, ppt2, palmitoyl-protein thioesterase |
| TE21 | A, B, E | apt1, apt2, acyl-protein thioesterase, phospholipase, carboxylesterase |
| TE22 | A, B, E | S-formylglutathione hydrolase, esterase A, esterase D |
| TE23 | A, B, E | Hydroxyglutathione hydrolase, glyoxalase II |

[a]A, archaea; B, bacteria; E, eukaryota. Most prevalent producers bolded

The TE from *Umbellularia californica*, which primarily hydrolyzes lauroyl-ACP may be selected as a suitable TE for two reasons. First, it provided FFA titers significantly higher than other acyl-ACP thioesterases, with titers of C12 to C14 species of approximately 180 mg/L. Secondly, the product would be undecane, and the products of in vivo esterification would be lauric acid methyl or ethyl esters, both of which should exhibit desirable properties as diesel fuel replacements or as components in diesel blends.

The process involves performing traditional cultures using industrial organisms (such as *E. coli, S. cerevisiae*, or *Pichia pastoris*) that convert various carbon sources (such as glucose, xylose, or glycerol) into chemical products through the operation of modified fatty acid biosynthesis with ACP-dependent thiolases. These organisms are considered workhorses of modern biotechnology, and are easy to genetically engineer, and scale up for industrial production levels of desired products.

The pathways in a living system are generally made by transforming the microbe with an expression vector encoding one or more of the proteins, but the genes can also be added to the chromosome by recombineering, homologous recombination, and similar techniques. Where the needed protein is endogenous, as is the case in some instances (e.g., FAS enzymes), it may suffice as is, but it is usually overexpressed using an inducible promoter for better functionality and user-control over the level of active enzyme.

As used herein, the expressions "microorganism," "microbe," "strain" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 50% identity to one of the listed sequences and also having the same general catalytic activity. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List_of_sequenced_bacterial_genomes.

Additionally, yeast, such as *Saccharomyces*, are a common species used for microbial manufacturing, and many species can be successfully transformed. Indeed, yeast are already available that express recombinant thioesterases—one of the termination enzymes described herein—and the reverse beta oxidation pathway has also been achieved in yeast. Other species include but are not limited to *Candida, Aspergillus, Arxula adeninivorans, Candida boidinii, Hansenula polymorpha (Pichia angusta), Kluyveromyces lactis, Pichia pastoris*, and *Yarrowia hpolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genetics of an organism was intentionally manipulated in some way.

"Reduced activity" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like. All reduced activity genes or proteins are signified herein by "−".

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any detectable expression in a species that lacks the activity altogether. Preferably, the activity is increased 100-500% or even ten-fold. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids or other vectors that exist in hundreds of copies in the cell may be preferred due to its simplicity and ease of exerting externals controls, although permanent modifications to the genome may be preferred in the long term for stability reasons.

The terms "operably associated" or "operably linked," as used herein, refer to functionally coupled nucleic acid sequences.

As used herein "recombinant" is relating to, derived from, or containing genetically engineered material. In other words, the genome was intentionally manipulated by the hand of man in some way.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to Escherichia, but a plasmid expressing a gene from E. coli or would be considered to be endogenous to any genus of Escherichia, even though it may now be overexpressed.

"Expression vectors" are used in accordance with the art accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand of man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The following abbreviations are used herein:

| ABBREVIATION | TERM |
|---|---|
| Box-R | Beta oxidation pathway in reverse. |
| FAS | Fatty acid biosynthesis |
| ACP | acyl carrier protein |
| TE | Thioesterase |

BRIEF DESCRIPTION OF THE DRAWINGS

FIG. 9A-D. A partial listing of preferred embodiments, and one or more of which can be combined with any other one or more.

DETAILED DESCRIPTION

Figure 1A:
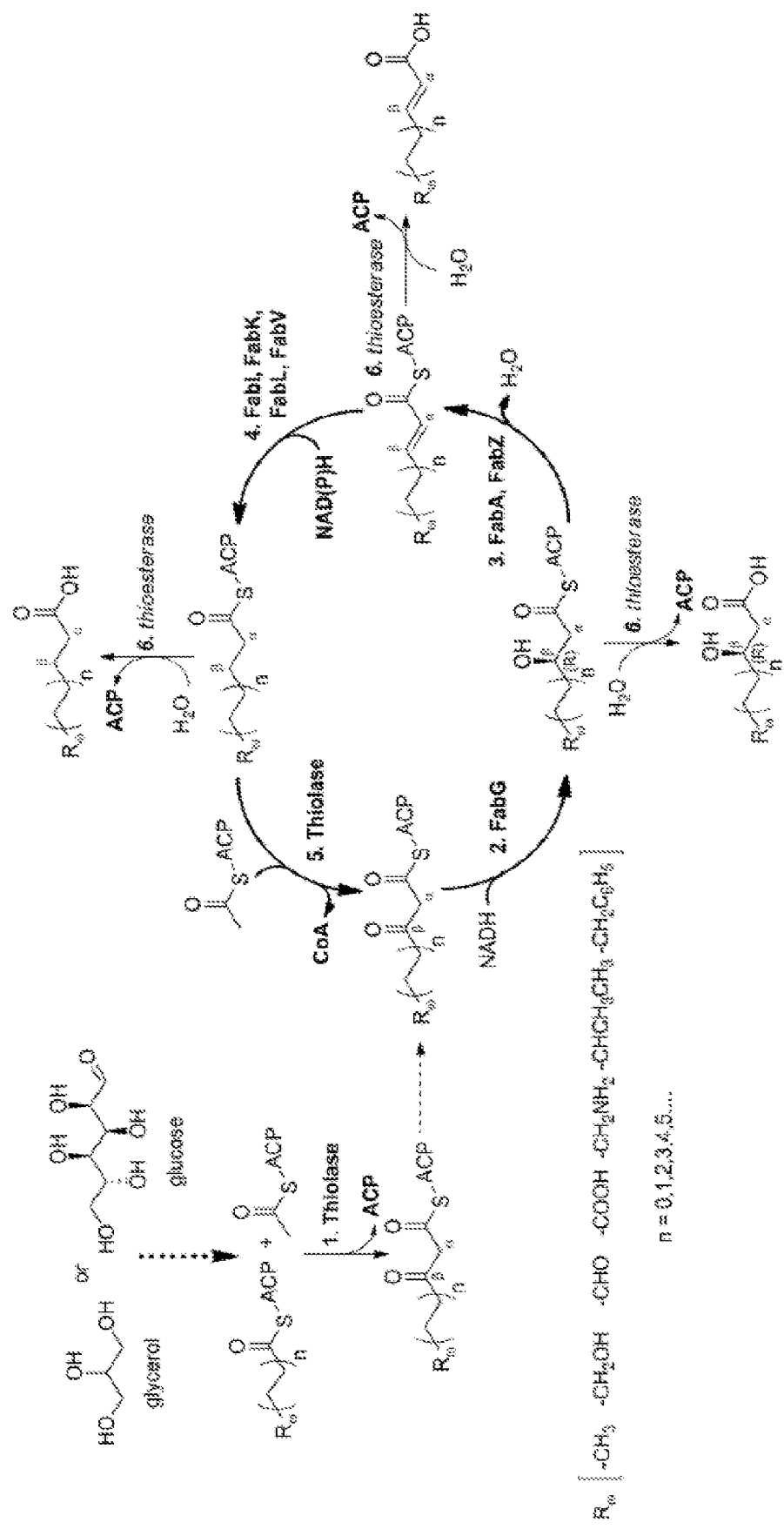
FIG. 1A. Modified FAS cycle with a native or engineered ACP-dependent thiolase(s) catalyzing the non-decarboxylative condensation of an acyl-ACP primer with 2-carbon donor acetyl-ACP to produce a β-ketoacyl-ACP; FabG: example of overexpressed 3-oxoacyl-[acyl-carrier-protein] reductase that catalyzes the reduction of a β-ketoacyl-ACP to a (3R)-β-hydroxyacyl-ACP; FabA, FabZ: examples of overexpressed 3-hydroxyacyl-[acyl-carrier-protein] dehydratases that catalyze the dehydration of a (3R)-β-hydroxyacyl-ACP to a trans-enoyl-ACP; FabI, FabK, FabL, FabV: examples of overexpressed enoyl-[acyl-carrier-protein] reductases that catalyze the reduction of a trans-enoyl-ACP to an acyl-ACP; Thioesterase: example of overexpressed termination pathway.

The technology herein is based on developing an alternative strategy to the efficient production of α-, β-, and ω-functionalized carboxylic acids, alcohols, hydrocarbons, and amines that focuses on the use of a native or engineered ACP-dependent thiolase in combination with type II fatty acid biosynthesis pathway genes/enzymes in *E. coli* and *S. cerevisiae* (as examples) to assemble a more ATP-efficient type II fatty acid biosynthesis pathway.

The thiolases described herein are enzymes capable of performing a non-decarboxylative condensation between a growing acyl-(acyl-carrier-protein) (acyl-ACP) and acetyl-ACP to form a β-ketoacyl-ACP 2 carbons longer than the starting acyl-ACP.

The bacterial type II fatty acid biosynthesis system has been harnessed for the synthesis of numerous products, including fatty acids, fatty acid methyl esters, fatty acid ethyl esters, fatty alcohols, and alkanes. At the core of this system is an elongation cycle that uses discrete enzymes to catalyze each of its four steps.

The native pathway is initiated by the condensation of malonyl-acyl carrier protein (ACP) with acyl-ACP, catalyzed by a 3-ketoacyl-ACP synthase. The resulting 3-ketoester is dehydrogenated by a 3-ketoacyl-ACP reductase followed by the dehydration of the resulting 3-R-hydroxyacyl-ACP to trans-2-enoylacyl-ACP. The enzymes catalyzing these three steps are relatively conserved among bacteria. However, at least four different enoyl-ACP reductase (ENR) bacterial families (FabI, FabL, FabV, and FabK) catalyze the last step of the cycle in which the trans-2-enoyl-ACP is reduced to an acyl-ACP. These include *E. coli* FabI, *Bacillus subtilis* FabL, *Vibrio cholerae* FabV, and *Enterococcus faecalis* FabK. Each elongation round uses malonyl-ACP as extender unit, and hence requires the ATP dependent conversion of acetyl-CoA to malonyl-CoA:

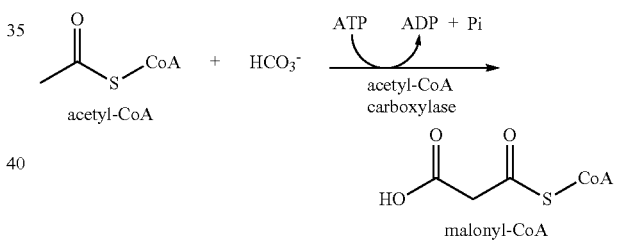

Technologies developed prior to this are based on the native version of the FAS pathway. However, the requirement for ATP consumption in the generation of the extender unit during the operation of this pathway dictates that the ATP yield associated with the production of products through the FAS pathway is very low. This, in turn, greatly limits cell growth and production of desired products.

While a functional reversal of the β-oxidation cycle has been exploited as one way of improving the energy efficiency of fatty acid synthesis, an alternative approach to overcoming the low ATP yield with the fatty acid synthesis pathway is circumventing the requirement of malonyl-ACP synthesis altogether. This requires the use of elongation mechanism involving a non-decarboxylative condensation, which can directly use acetyl-ACP as the extender unit, avoiding the ATP consumption during the carboxylation of acetyl-CoA via acetyl-CoA carboxylase to form malonyl-CoA, which is subsequently converted to malonyl-ACP.

This type of condensation mechanism is employed by the thiolase enzymes involved in the degradation of fatty acids, which have been shown to function in the biosynthetic direction during a beta-oxidation reversal. Thus, any of the thiolases described above, can be used for the opposite reaction merely by building up the substrates or enzyme levels (or both) so as to drive the reaction in the forward biosynthetic direction, provided the enzyme has a suitable substrate specificity.

Key to this approach is the use of native or engineered ACP-dependent thiolases capable of performing a non-decarboxylative condensation between a growing acyl-(acyl-carrier-protein) (acyl-ACP) and acetyl-ACP to form a β-ketoacyl-ACP 2 carbons longer than the starting acyl-ACP. Many examples of thiolase enzymes which can potentially catalyze the non-decarboxylative condensation of an acyl-ACP primer and acetyl-ACP extender unit are provided herein and Table A provides several additional examples which can also serve as templates for engineered variants. Additional examples can be found by linkage in suitable databases (e.g., UniProt, Brenda, and the like), by EC number, or by homology search, and the activity easily confirmed once the protein is made.

Through the use of native or engineered thiolase(s) capable of condensing an acyl-ACP and acetyl-ACP in a non-decarboxylative fashion, the energy (ATP) intensive steps of the fatty acid biosynthesis pathway can be bypassed, as acetyl-ACP can be utilized as the extender unit as opposed to malonyl-ACP, whose synthesis from acetyl-CoA requires ATP. As such, this native or engineered ACP-dependent thiolase will form a β-ketoacyl-ACP 2 carbons longer than the starting acyl-ACP, which can then be converted into the corresponding acyl-ACP through the action of the ubiquitous type II fatty acid biosynthesis enzymes 3-oxoacyl-[acyl-carrier-protein] reductase (FabG, others), 3-hydroxyacyl-[acyl-carrier-protein] dehydratase (FabA, FabZ, others), and enoyl-[acyl-carrier-protein] reductase (FabI, FabK, FabL, FabV, others) (FIG. 1A).

Figure 1B:
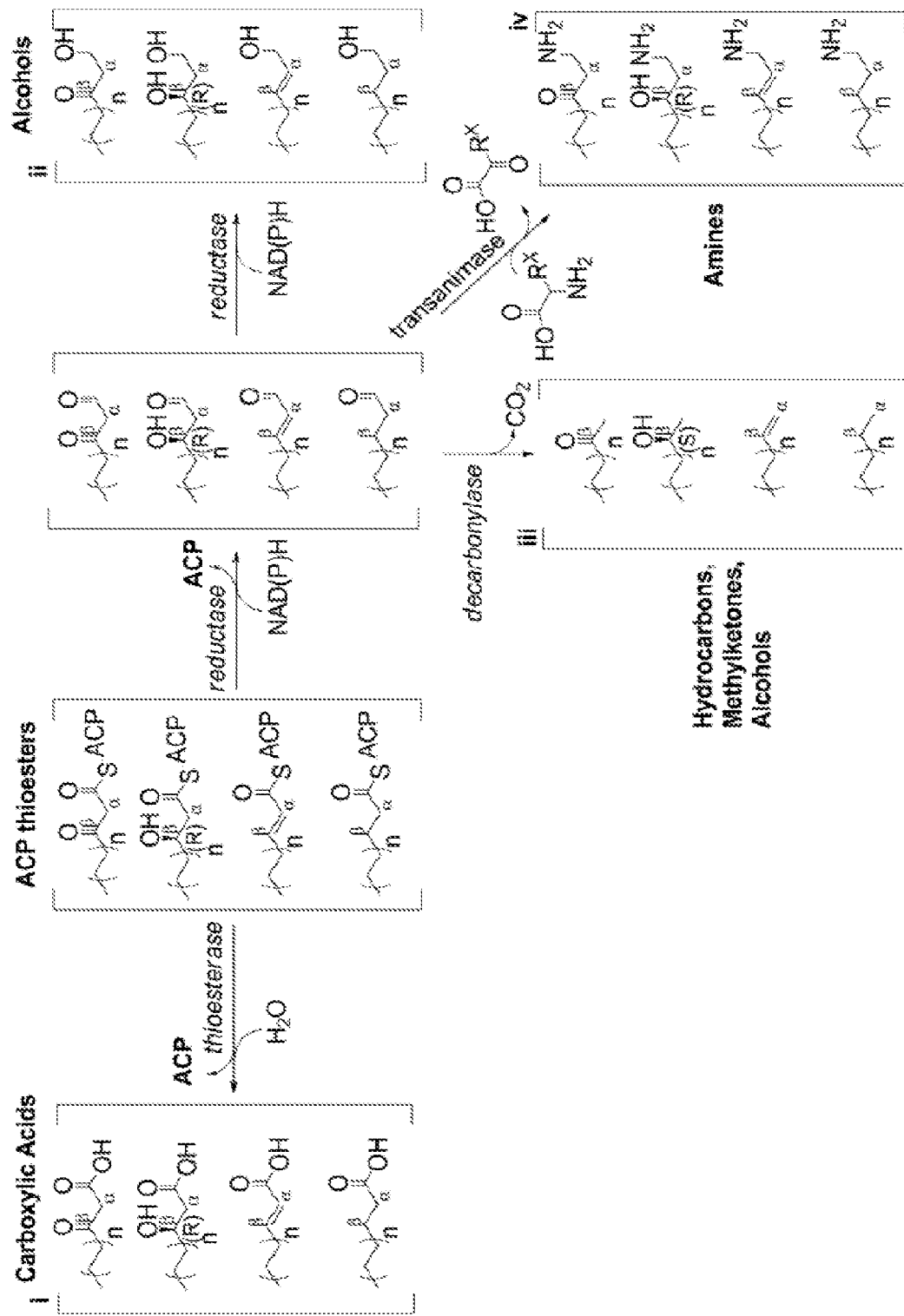
FIG. 1B. Primary termination pathways. Pathways that act on the ACP thioester group/carbon, resulting in the synthesis of i) carboxylic acids, ii) primary alcohols, iii) hydrocarbons, and iv) primary amines, along with their ß-hydroxy, ß-keto, and α,β-unsaturated derivatives are illustrated.
Figure 1C:
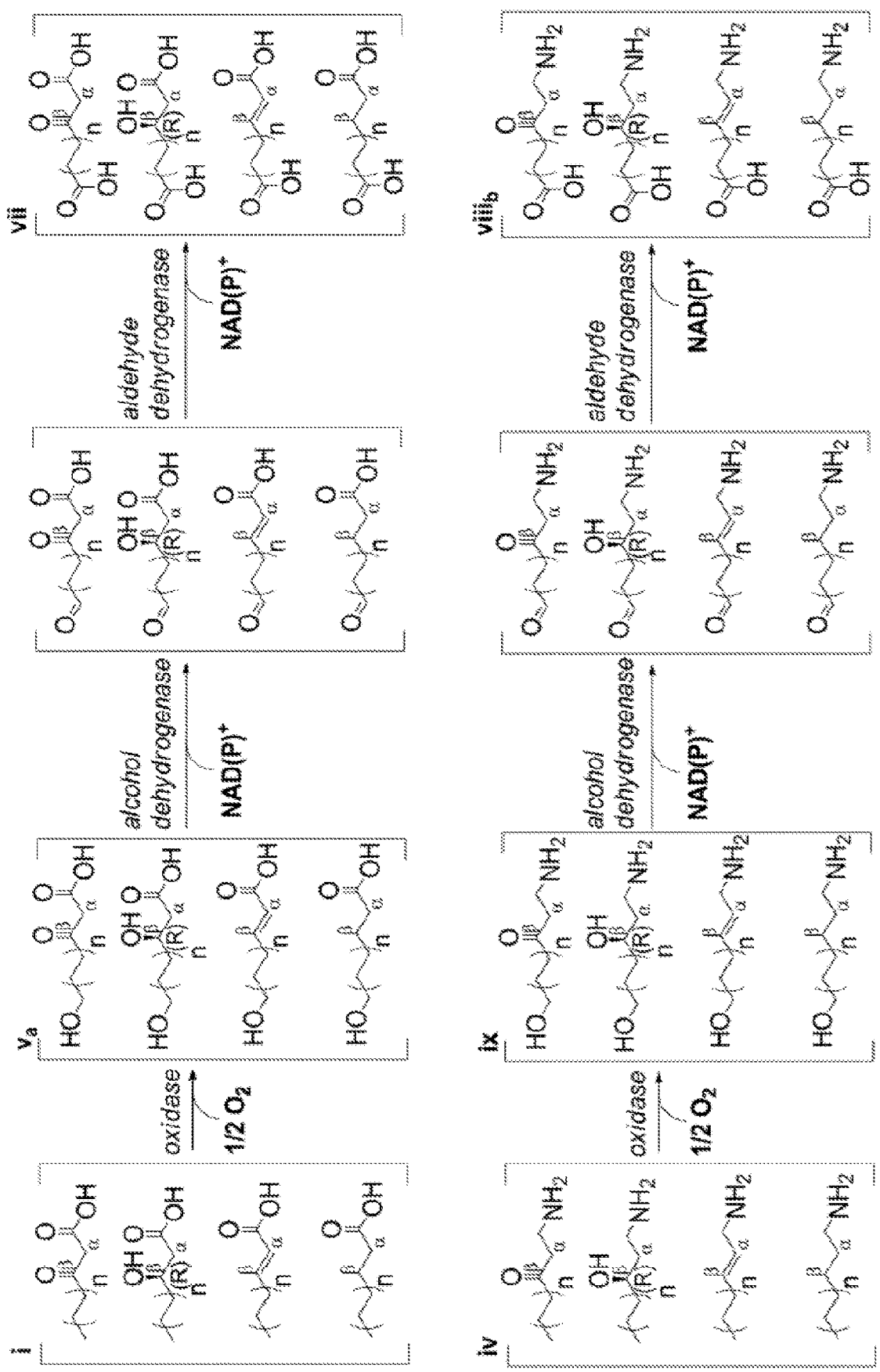
FIG. 1C. Secondary termination pathways continuing from the primary pathways shown in FIG. 1B. Pathways for the production of omega-hydroxylated carboxylic acids ($v_a$), dicarboxylic acids (vii), omega-hydroxylated primary amines (ix), and omega carboxylic acid primary amines ($viii_b$) along with their ß-hydroxy, ß-keto, and α,β-unsaturated derivatives from the carboxylic acids (i) and primary amines (iv) generated from FAS with primary termination pathways are illustrated.
Figure 1D:
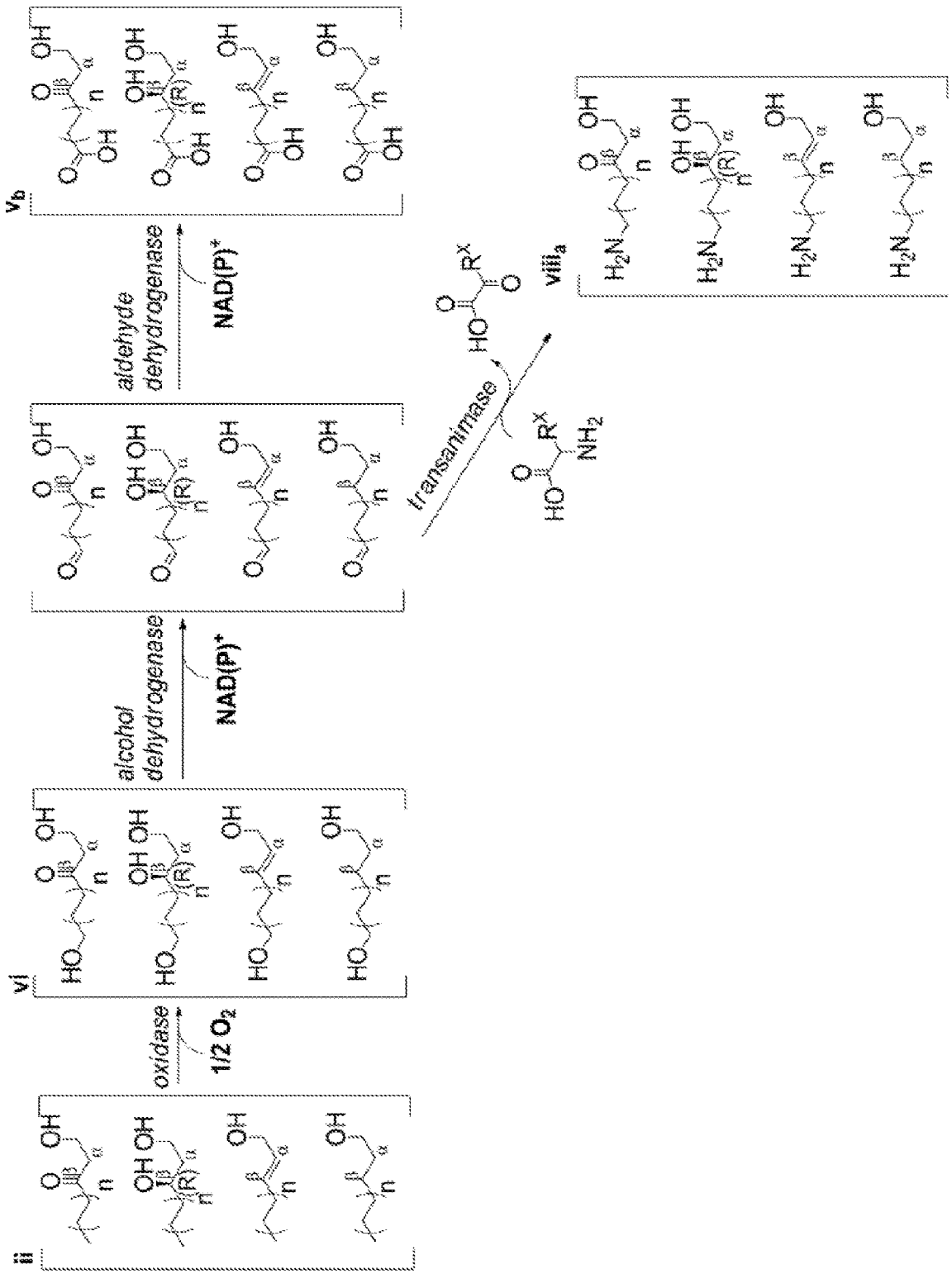
FIG. 1D. Secondary termination pathways. Pathways for the production of omega-hydroxylated primary alcohols (vi), omega carboxylic acid primary alcohols ($v_b$), and omega amino primary alcohols ($viii_a$) along with their ß-hydroxy, ß-keto, and α,β-unsaturated derivatives from the primary alcohols (ii) generated from FAS with primary termination pathways are illustrated.
Figure 1E:
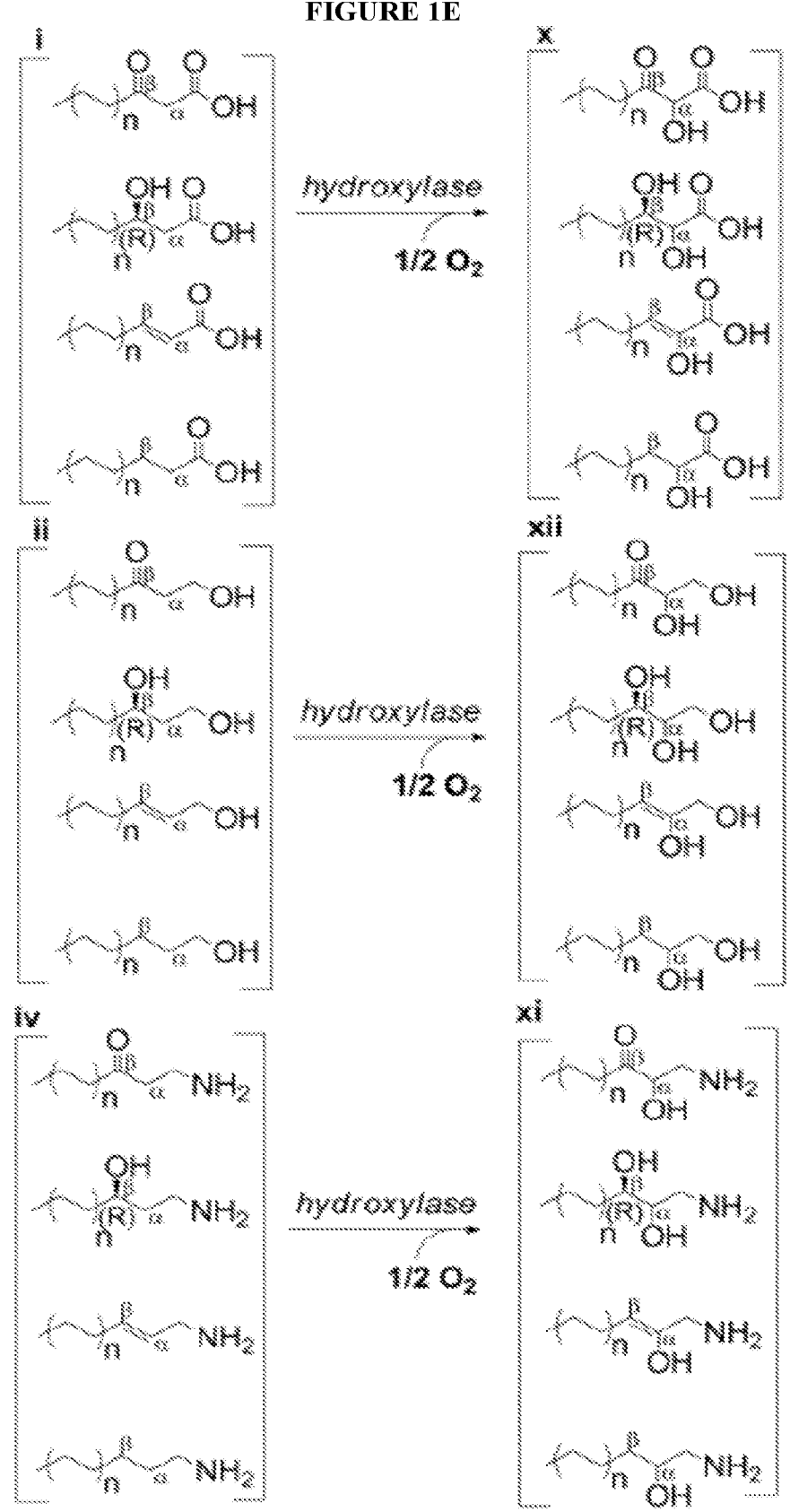
FIG. 1E. Secondary termination pathways. Pathways for the production of alpha-hydroxylated carboxylic acids (x), alpha-hydroxylated primary alcohols (xii), and alpha-hydroxylated primary amines (xi) along with their ß-hydroxy, ß-keto, and α,β-unsaturated derivatives from the carboxylic acids (i), primary alcohols (ii), and primary amines (iv), generated from FAS with primary termination pathways are illustrated.

Continued elongation cycles along with overexpression of one or more termination enzymes that convert ACP intermediates to desired products, such as those currently produced from the FAS cycle, provide the ability to synthesize a wide range of products with higher ATP yields, critical to maximizing product titer, yield, and productivity. Furthermore, any of the products, such as alcohols, carboxylic acids, etc., produce via these primary termination pathways (FIG. 1B) can be further modified to make other products in secondary termination pathways (FIG. 1C, FIG. 1D, FIG. 1E).

In summary, the recombinant engineering required to utilize acyl-carrier-protein (ACP)-dependent thiolases in iterative pathways for the synthesis of higher chain higher-chain (C≥4) products is:

1) Expression or overexpression of native or engineered thiolases capable of performing a non-decarboxylative condensation between a growing acyl-ACP and acetyl-ACP. This represents the key step in enabling a more energy efficient fatty acid biosynthesis pathway. The use of a native or engineered thiolase condensing an acyl-ACP and acetyl-ACP in a non-decarboxylative fashion will negate the use of malonyl-ACP during the traditional decarboxylative condensation employed during FAS elongation. Non-decarboxylative condensation between the extender unit acetyl-ACP and the acyl-ACP primer, as well as the growing acyl-ACP following elongation cycles, will result in the addition of 2 carbons per cycle, with the resulting β-ketoacyl-ACP intermediate able to go through subsequent reduction, dehydration, and reduction steps via enzymes described below.

2) Functional operation of the additional fatty acid biosynthesis steps for the reduction, dehydration, and second reduction of the β-ketoacyl-ACP formed the previous step. In addition to functionally expressing the ACP-dependent non-decarboxylative thiolase(s), 3-oxoacyl-[ACP]/β-ketoacyl-[ACP] reductase (FabG, others), 3-hydroxyacyl-[ACP] dehydratase (FabA, FabZ, others), and enoyl-ACP reductase (FabI, FabK, FabL, FabV, others) are also required to enable the generation of a diverse set of ACP thioester intermediates. See e.g., FIG. 1A. These three enzymes can be native enzymes, overexpressed native enzymes or exogenous enzymes, as desired. Preferably, they are overexpressed under an inducible promoter.

3) Conversion of ACP thioester intermediates to the desired end products. Generally speaking, there are several termination enzymes that will pull reaction intermediates out the fatty acid biosynthesis pathway and produce the desired end product (FIGS. 1B-E), and a nonexclusive list is provided in Table C.

One or more of these termination enzymes can be overexpressed, as needed depending on the desired end product. The termination enzymes can be native or non-native as desired for particular products. Preferably, they are overexpressed under an inducible promoter.

4) Regulation of product chain length. The chain length of thioester intermediates determines the length of end products, and can be controlled by using appropriate termination enzymes with the desired chain-length specificity. Additionally, chain elongation can be inhibited or promoted by reducing or increasing the activity of thiolases with the desired chain-length specificity. These two methods can be used together or independently.

The following description provides additional details, any one of which can be subject to patenting in combination with any other. The specification in its entirety is to be treated as providing a variety of details that can be used interchangeably with other details, as the specification would be of inordinate length if one were to list every possible combination of genes/vectors/enzymes/hosts that can be made to enable carbon source conversion to desired fuels and chemicals of interest through a modified fatty acid biosynthesis pathway with ACP-dependent thiolases.

Enzymes of interest can be expressed from vectors such as pETDuet-1 or pCDFDuet-1 (MERCK, Germany), which makes use of the DE3 expression system. Genes can be codon optimized according to the codon usage frequencies of the host organism and synthesized by a commercial vendor or in-house. However, thousands of expression vectors and hosts are available, and this is a matter of convenience.

The genes can be amplified by PCR using primers designed with 15-22 base pairs of homology for the appropriate vector cut site. For enzymes that will not require a 6×-histidine tag fusion for purification, pCDFDuet-1 can be linearized with NcoI and EcoRI. Enzymes that will be purified by Ni-NTA column will make use of the 6×-HIS tag in pCDFDuet-1. The vector can be linearized using only EcoRI in this case.

The PCR product can be inserted into the vector using e.g., the In-Fusion HD EcoDry Cloning System and the vector transformed by heat shock into competent E. coli cells. Transformants can be selected on solid media containing the appropriate antibiotic. Plasmid DNA can be isolated using any suitable method, including QIAprep Spin Miniprep Kit (QIAGEN, Limburg), and the construct confirmed by PCR and sequencing. Confirmed constructs can be transformed by e.g., electroporation into a host strain such as E. coli for expression, but other host species can be used with suitable expression vectors and possible codon optimization for that host species.

Expression of the desired enzymes from the constructed strain can be conducted in liquid culture, e.g., shaking flasks, bioreactors, chemostats, fermentation tanks and the like. Gene expression is typically induced by the addition of a suitable inducer, when the culture reaches an $OD_{550\,nm}$ of approximately 0.5-0.8. Induced cells can be grown for about 4-8 hours, at which point the cells can be pelleted and saved to −20° C. Expression of the desired protein can be confirmed by running samples on SDS-PAGE.

The expressed enzyme can be directly assayed in crude cell lysates, simply by breaking the cells by chemical, enzymatic, heat or mechanical means. Depending on the expression level and activity of the enzyme, however, purification may be required to be able to measure enzyme activity over background levels. Purified enzymes can also allow for the in vitro assembly of the pathway, allowing for its controlled characterization.

N- or C-terminal HIS-tagged proteins can be purified using e.g., a Ni-NTA Spin Kit (Qiagen, Venlo, Limburg) following the manufacturer's protocol, or other methods could be used. The HIS-tag system was chosen for convenience only, and other tags are available for purification uses. Further, the proteins in the final assembled pathway need not be tagged if they are for in vivo use. Tagging was convenient, however, for the enzyme characterization work performed hereunder.

Reaction conditions for enzyme assays can vary greatly with the type of enzyme to be tested. In general, however, enzyme assays follow a similar general protocol. Purified enzyme or crude lysate is added to suitable reaction buffer. Reaction buffers typically contain salts, necessary enzyme cofactors, and are at the proper pH. Buffer compositions often change depending on the enzyme or reaction type. The reaction is initiated by the addition of substrate, and some aspect of the reaction related either to the consumption of a substrate or the production of a product is monitored.

As an example, cultures for enzymatic assays were conducted in 125 mL Erlenmeyer flasks containing 25 mL LB media inoculated at 3% from an overnight culture. E. coli strains containing constructs expressing genes of interest were grown under appropriate conditions until an optical density of ~0.5 was reached, at which point inducer(s) were added and the cells incubated for an additional 4 hrs. Cell harvesting and preparation of crude cell extracts for enzyme assays was conducted as described elsewhere (Dellomonaco et al., 2011). Enzymatic reactions were then monitored on either a Synergy HT plate reader (BioTek Instruments, Inc., Winooski, Vt.) or a Biomate 5 Spectrophotometer (Thermo Scientific, Waltham, Mass.) according to established protocols.

Degradative thiolase activity was determined in a reaction mixture containing 100 mM Tris HCl (pH 8.0), 1 mM DTT, and 10 mM $MgCl_2$. Measurement of thiolase activity with ACP intermediates utilized 0.1 mM acetoacetyl-ACP and 0.2 mM holo-ACP, and followed the loss of acetoacetyl-ACP as measured by absorbance of the enol form at 303 nm. Activity was calculated using an extinction coefficient of 14 $mM^{-1}\,cm^{-1}$.

Acetoacetyl-ACP reductase (FabG) activity was measured in a reaction mixture containing 100 mM Tris HCl (pH 8.0), 1 mM DTT, 10 mM $MgCl_2$, 0.2 mM NADPH, and 75 11M acetoacetyl-ACP by following the oxidation of NADPH at an absorbance of 340 nm. Activity was calculated using an extinction coefficient of 6.2 $mM^{-1}\,cm^{-1}$.

Synthetic thiolase activity was determined in a reaction mixture containing 100 mM Tris HCl (pH 8.0), 1 mM DTT, 10 mM $MgCl_2$, 0.2 mM NADPH, ~55 mg/L purified FabG, and 2 mM acetyl-ACP. Activity was measured following the oxidation of NADPH at an absorbance of 340 nm, a result of the reduction of acetoacetyl-ACP formed from the condensation of 2 acetyl-ACP molecules. For all assays, an appropriate amount of enzyme was added to establish the linearity of reaction.

Once pathways have been fully studied in vitro, they can be constructed in vivo with greater confidence. The strain construction for the in vivo pathway operation should allow for the well-defined, controlled expression of the enzymes of the pathway. As before, E. coli or yeast will be a host of choice for the in vivo pathway, but other hosts could be used. The Duet system, for example, allows for the simultaneous expression of up to eight proteins by induction with IPTG in E. coli, and initial experiments will use this host.

Pathway enzymes can also be inserted into the host chromosome, allowing for the maintenance of the pathway without requiring antibiotics to ensure the continued upkeep of plasmids. A large number of genes that can be placed on the chromosome, as chromosomal expression does not require separate origins of replication as is the case with plasmid expression.

DNA constructs for chromosomal integration usually include an antibiotic resistance marker with flanking FRT sites for removal, as described by Datsenko and Wanner (2000), a well characterized promoter, a ribosome binding site, the gene of interest, and a transcriptional terminator. The overall product is a linear DNA fragment with 50 base pairs of homology for the target site on the chromosome flanking each side of the construct.

However, the Flp-FRT recombination method is only one system for adding genes to a chromosome, and other systems are available, such as the RecBCD pathway, the RecF pathway, RecA recombinase, non-homologous end joining (NHEJ), Cre-Lox recombination, TYR recombinases and integrases, SER resolvases/invertases, SER integrases, PhiC31 Integrase, and the like. Chromosomal modifications in E. coli can also achieved by the method of recombineering, as originally described by Datsenko and Wanner (2000).

In a recombineering method, for example, the cells are prepared for electroporation following standard techniques, and the cells transformed with linear DNA that contains flanking 50 base pair targeting homology for the desired modification site. For seamless integration of a DNA construct, a two-step approach can be taken using a cassette that contains both positive and negative selection markers, such as the combination of cat and sacB. In the first round of recombineering, the cat-sacB cassette with targeting homology for the desired modification site is introduced to the cells. The cat gene provides resistance to chloramphenicol, which allows for positive recombinants to be selected for on solid media containing chloramphenicol.

A positive isolate can be subjected to a second round of recombineering introducing the desired DNA construct with targeting homology for sites that correspond to the removal of the cat-sacB cassette. The sacB gene encodes for an enzyme that provides sensitivity to sucrose. Thus, growth on media containing sucrose allows for the selection of recombinants in which the cat-sacB construct was removed. P1 phage lysates can be made from isolates confirmed by PCR and sequencing. The lysates can be used to transduce the modification into desired strains, as described previously.

Engineered strains expressing the modified pathway can be cultured under the following or similar conditions. Overnight cultures started from a single colony can be used to inoculate flasks containing appropriate media. Cultures are grown for a set period of time, and the culture media analyzed. The conditions will be highly dependent on the specifications of the actual pathway and what exactly is to be tested. For example, the ability for the pathway to be used for hydrocarbon utilization can be tested by the use of short-chain alkanes as a substrate in MOPS minimal media, as described by Neidhardt et al (1974), supplemented with appropriate antibiotics, and inducers.

Analysis of culture media after fermentation provides insight into the performance of the engineered pathway. Quantification of hydrocarbons and longer chain fatty acid and alcohol products can be analyzed by GC. Other metabolites, such as short chain organic acids and alcohols can be analyzed by high pressure liquid chromatograph (HPLC). Once the pathway is fully functional, the cultures can be grown in chemostat, providing continuous uninterrupted production of product if desired.

Various-omics techniques, such as microarray or 2D-PAGE can give information about gene expression or protein expression, respectively. Genome scale modeling allows for the identification of additional modifications to the host strain that might lead to improved performance. Deletion of competing pathways, for example, might increase carbon flux through the engineered pathway for product production.

Standard molecular biology techniques were used for gene cloning, plasmid isolation, and $E.\ coli$ transformation. Native $E.\ coli$ genes were amplified from $E.\ coli$ MG1655 genomic DNA using primers to append 15 bp of homology on each end of the gene insert for recombination into the vector backbone. Genes from other organisms were codon optimized and synthesized by either GeneArt (LIFE TECH., CA or GENSCRIPT, NJ). Plasmids were linearized by the appropriate restriction enzymes and recombined with the gene inserts using the In-Fusion HD Eco-Dry Cloning system (CLONTECH LAB. CA,). The mixture was subsequently transformed into Stellar competent cells (CLONTECH LAB.).

Transformants that grew on solid media (LB+Agar) supplemented with the appropriate antibiotic were isolated and screened for the gene insert by PCR. Plasmid was isolated from the verified transformants and the sequence of the gene insert was further confirmed by DNA sequencing (LONE STAR LABS, TX). Plasmids (also referred to as vectors) in each case contain at least one promoter, a ribosome binding site for each gene, the gene(s) of interest, at least one terminator, an origin of replication, and an antibiotic resistance marker.

Figure 2:
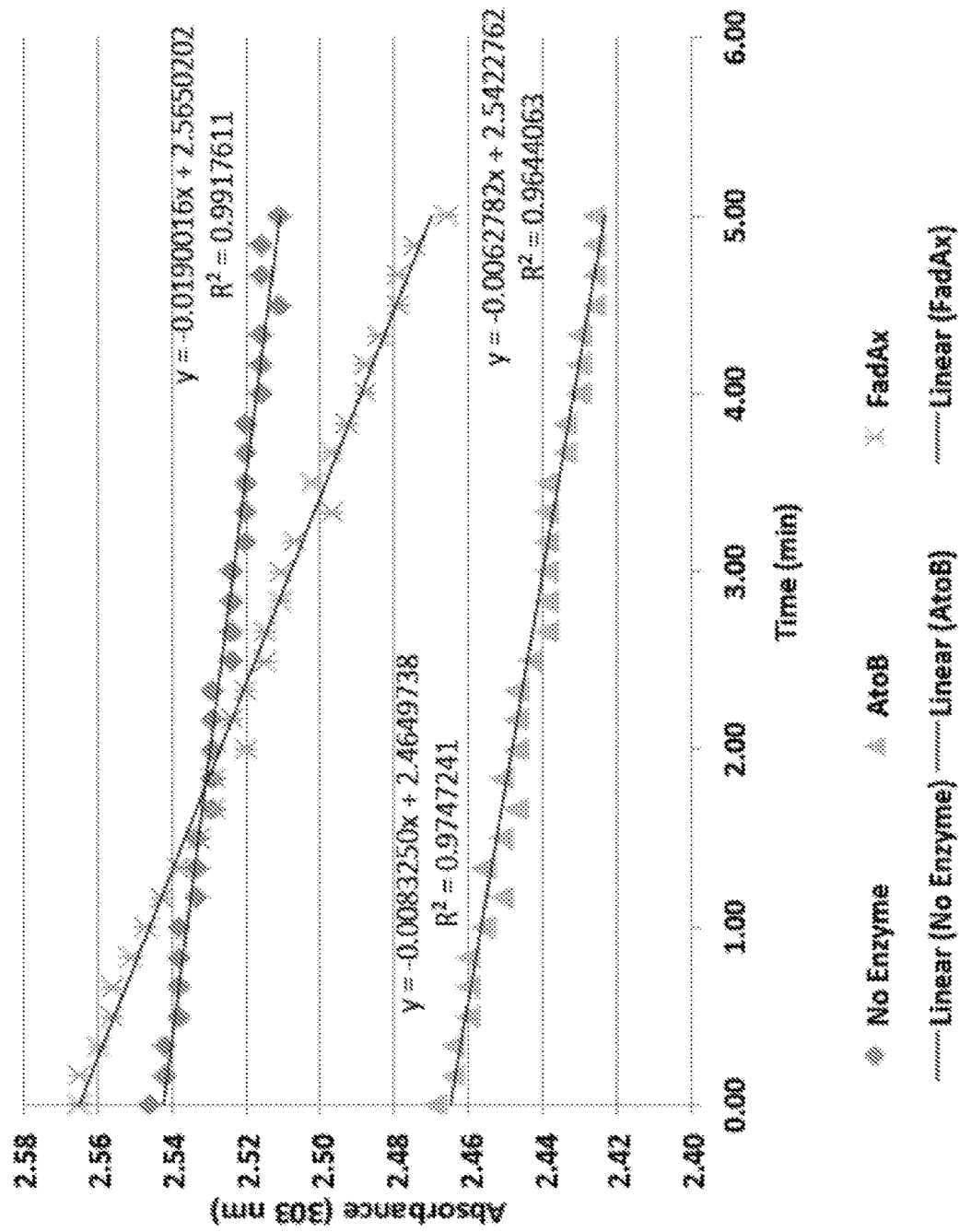
FIG. 2. Thiolase (AtoB or FadAx) catalyzed acetoacetyl-ACP degradation. Time course absorbance at 303 nm shown for reaction mixtures containing 100 mM Tris HCl (pH 8.0), 1 mM DTT, 10 mM MgCl$_2$, 0.2 mM holo-ACP, and 0.1 mM acetoacetyl-ACP with purified AtoB, FadAx, or no enzyme control.
Figure 3:
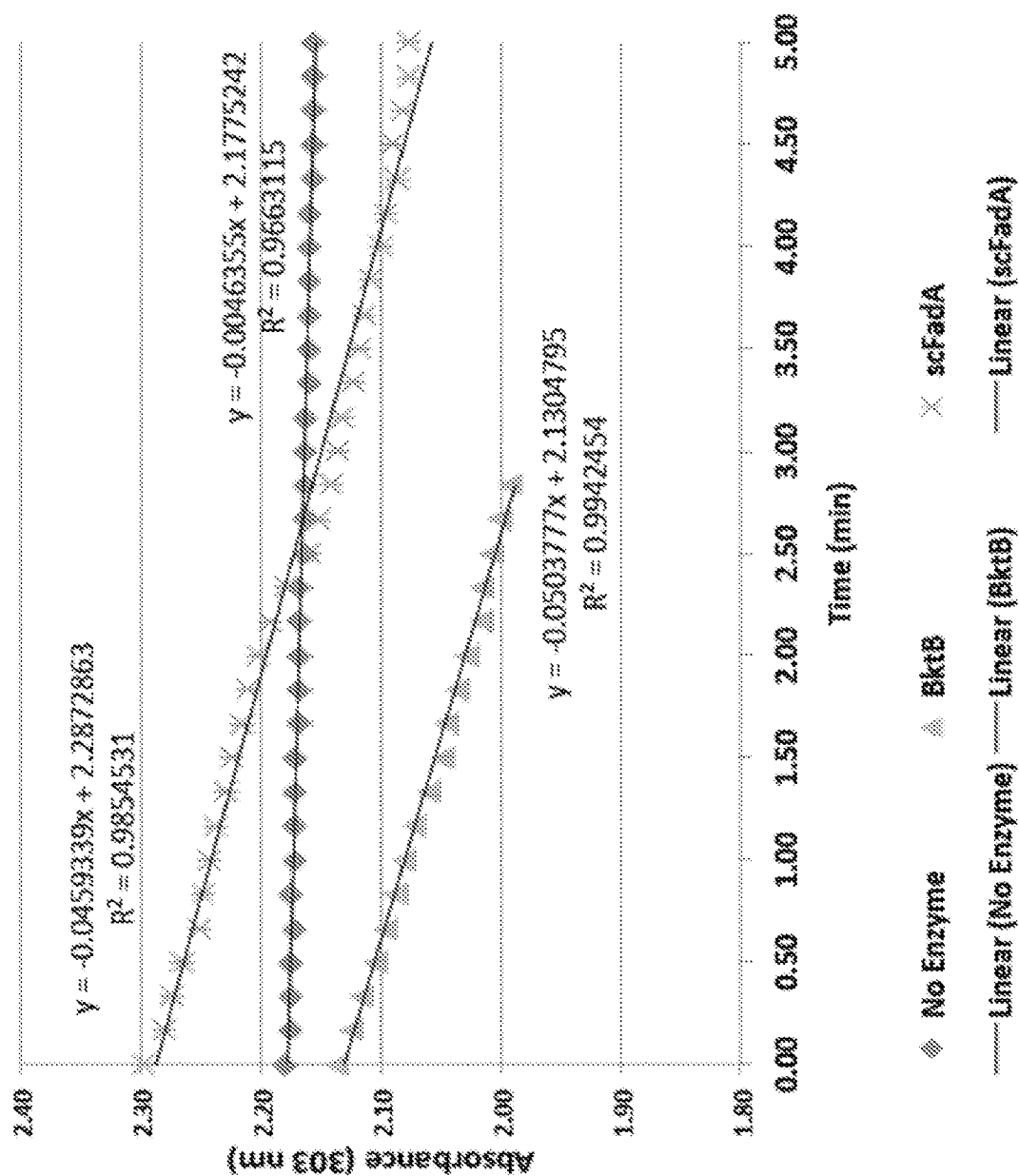
FIG. 3. Thiolase (BktB or scFadA) catalyzed acetoacetyl-ACP degradation. Time course absorbance at 303 nm shown for reaction mixtures containing 100 mM Tris HCl (pH 8.0), 1 mM DTT, 10 mM MgCl$_2$, 0.2 mM holo-ACP, and 0.1 mM acetoacetyl-ACP with purified BktB, scFadA, or no enzyme control.

In order to establish the ability for thiolases to function with ACP-intermediates, as opposed to their physiological substrates (acyl-CoA's), genes that encode candidate thiolases were cloned and expressed as described above. Purified enzymes were then first assessed for their ability to catalyze the degradative thiolases reaction with acetoacetyl-ACP as the substrate. As shown in FIG. 2 and FIG. 3, thiolases AtoB, FadAx, BktB, and scFadA all lead to a decrease in absorbance at 303 nm, representing the consumption of acetoacetyl-ACP and demonstrating the function of these enzymes with this ACP substrate. The linearity of each reaction was established, and the respective specific activities for each enzyme is shown in TABLE E.

TABLE E

Specific thiolase activities for the degradation of acetoacetyl-ACP

| Thiolase | Specific activity (nmol/mg/min) |
|---|---|
| $E.\ coli$ AtoB | 34.8 |
| $P.\ putida$ FadAx | 19.3 |
| $R.\ eutropha$ BktB | 129.6 |
| $S.\ collinus$ FadA | 199.8 |

Figure 4:
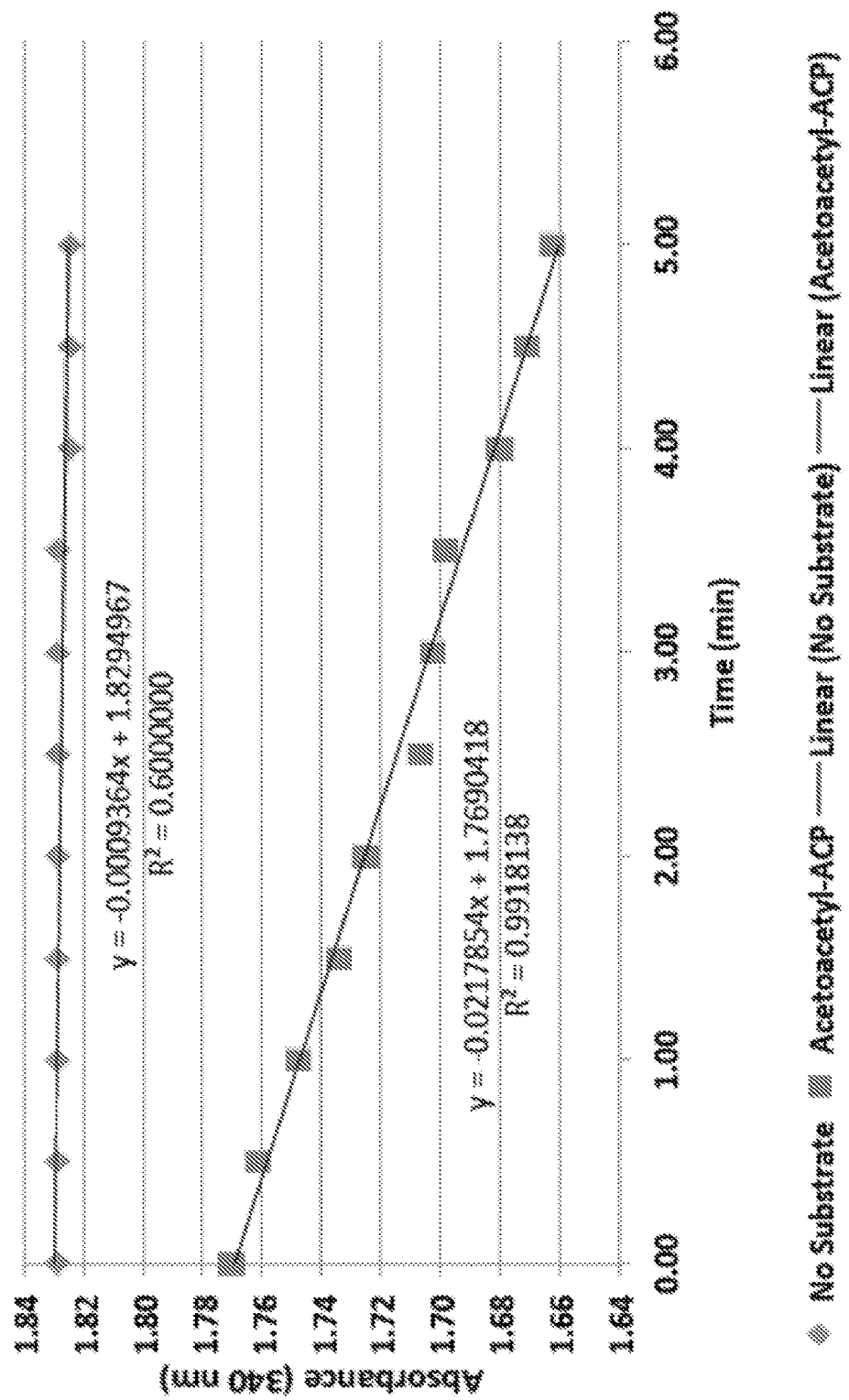
FIG. 4. NADPH-dependent reduction of acetoacetyl-ACP by FabG. Absorbance at 340 nm shown for reaction mixtures containing 100 mM Tris HCl (pH 8.0), 1 mM DTT, 10 mM MgCl$_2$, 0.2 mM NADPH, and 75 µM acetoacetyl-ACP with or without purified FabG.

The ability for these enzymes to function in the synthetic direction with ACP intermediates was established through a coupled assay in which the FabG mediated reduction of acetoacetyl-ACP formed following the thiolase catalyzed condensation of 2 molecules of acetyl-ACP. The reduction of acetoacetyl-ACP by FabG was first established (FIG. 4), with a specific activity of NADPH-dependent reduction of 0.44 µmol/mg/min calculated. In addition to providing a basis for measuring synthetic thiolase activity with ACP intermediates, this also demonstrates another key reaction of the cycle, which when combined with enzymes such as FabZ (Heath and Rock, 1996) and FabI (Bergler et al., 1996) forms the full set of beta-reduction required for the modified fatty acid biosynthesis pathway.

Figure 5:
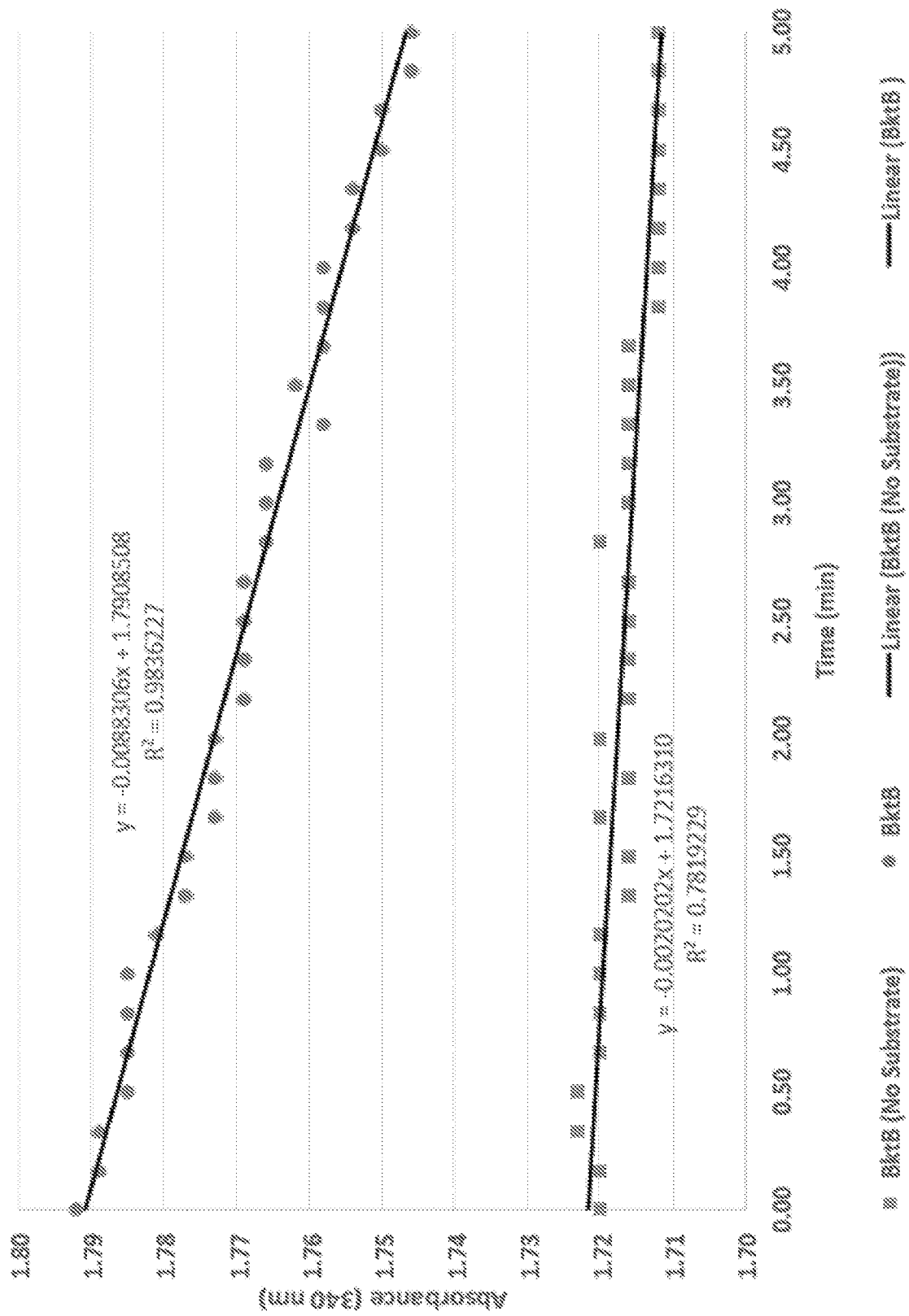
FIG. 5. Non-decarboxylative condensation of acetyl-ACP mediated by ACP-dependent thiolase BktB. Absorbance at 340 nm shown for reaction mixtures containing 100 mM Tris HCl (pH 8.0), 1 mM DTT, 10 mM MgCl$_2$, 0.2 mM NADPH, and ~55 mg/L purified FabG, with and without 2 mM acetyl-ACP. Activity was measured following the oxidation of NADPH, a result of the reduction of acetoacetyl-ACP formed from the condensation of 2 acetyl-ACP molecules.
Figure 6:
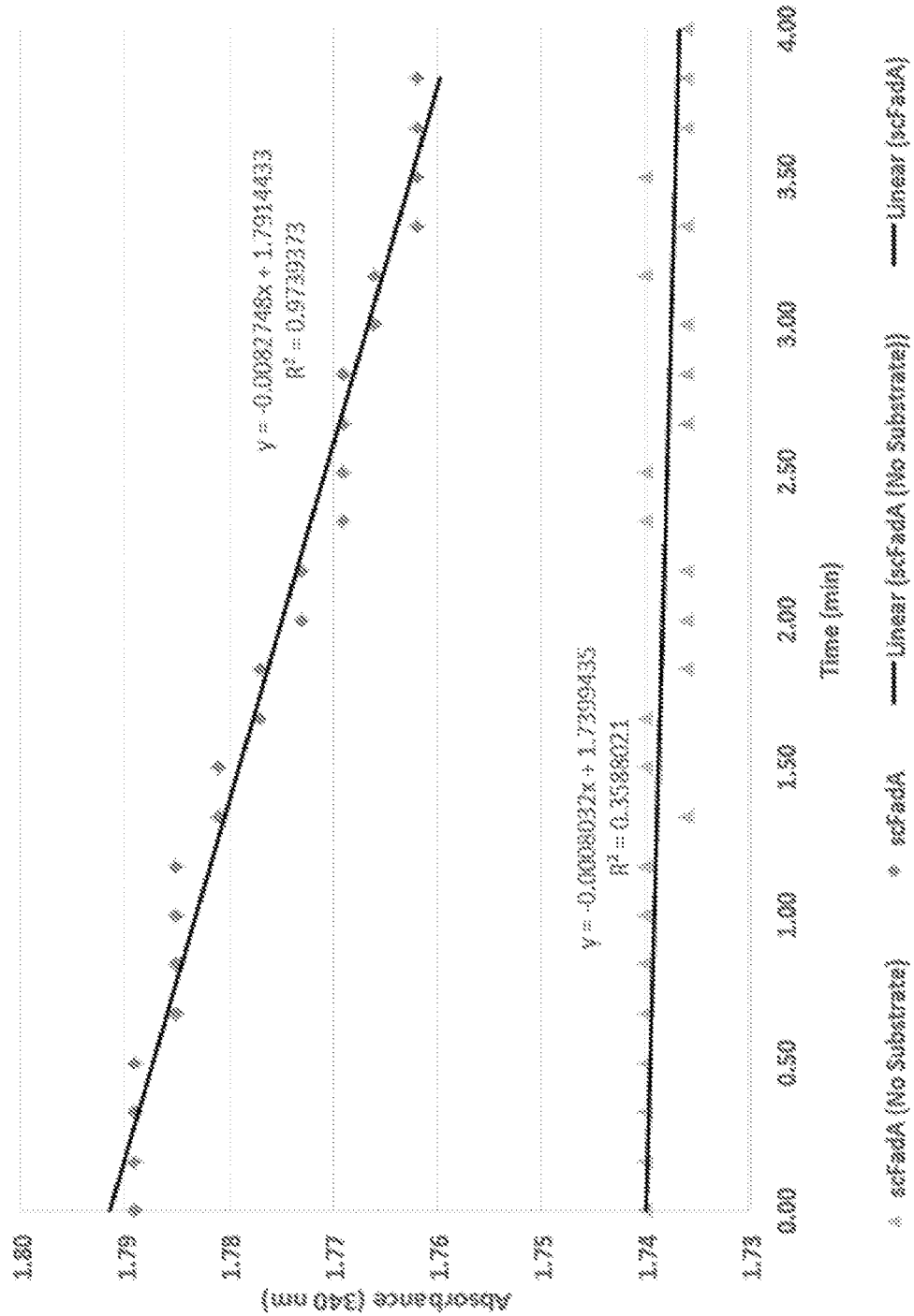
FIG. 6. Non-decarboxylative condensation of acetyl-ACP mediated by ACP-dependent thiolase scFadA. Absorbance at 340 nm shown for reaction mixtures containing 100 mM Tris HCl (pH 8.0), 1 mM DTT, 10 mM MgCl$_2$, 0.2 mM NADPH, and ~55 mg/L purified FabG, with and without 2 mM acetyl-ACP. Activity was measured following the oxidation of NADPH, a result of the reduction of acetoacetyl-ACP formed from the condensation of 2 acetyl-ACP molecules.

Using purified FabG, synthetic thiolase activity for the condensation of 2 molecules for acetyl-ACP was established for both BktB (FIG. 5) and scFadA (FIG. 6), in which the reduction of acetoacetyl-ACP, measured via oxidation of NADPH, formed from thiolase mediated condensation of acetyl-ACP was observed. The clearly establishes the novel ACP-dependent thiolase activity required for the modified fatty acid biosynthesis pathway described herein, and when combined with the required beta-reduction enzymes, forms a full pathway for the generation of longer chain length ACP intermediates that can be subsequently converted to products of interest.

Based on these findings, carboxylic acid synthesis through ACP-dependent thiolases and thioesterase termination was investigated through the expression of all pathway components in vivo. $S.\ collinus$ FadA (scFadA) was utilized as the ACP-dependent thiolase, given its reported ability to also function as an acetyl-CoA:ACP transacylase (Lobo et al., 2001) for the generation of acetyl-ACP required as a primer/extender for modified fatty acid biosynthesis with ACP-dependent thiolases. scFadA was integrated into the chromosome in place of atoB (acetyl-CoA acetyltransferase) as previously described (Clomburg et al., 2015) to enable inducible expression under cumate control.

Genes encoding representative fatty acid biosynthesis enzymes FabG, FabZ, and FabI from $E.\ coli$ K12 MG1655 were cloned into pETDuet-1 (pETDuet-1-P1-fabI-P2-fabG-fabZ) and genes encoding thioesterases demonstrated to function on short chain ACP intermediates (*Bacteroides thetaiotaomicron* bTE, *Bacteroides fragilis* Tes4, *Marvinbryantia formatexigens* BRYFOR_06758; Jing et al., 2011) were cloned into pCDFDuet-1 to enable IPTG inducible expression. These genetic constructs were combined as needed in JC01 (MG1655 ΔldhA ΔpoxB Δpta ΔadhE ΔfrdA) (DE3) and derivatives (strains with the scFadA chromosomal construct included deletions to fadB and fadJ).

The minimal medium designed by Neidhardt et al. (1974), with 125 mM MOPS and $Na_2HPO_4$ in place of $K_2HPO_4$, supplemented with 20 g/L glycerol, 10 g/L tryptone, 5 g/L yeast extract, 100 µM $FeSO_4$, 5 mM calcium pantothenate, 1.48 mM $Na_2HPO_4$, 5 mM $(NH_4)_2SO_4$, and 30 mM $NH_4Cl$ was used for all fermentations. Fermentations were conducted in 25 mL Pyrex Erlenmeyer flasks (Corning Inc., Corning, N.Y.) filled with 20 mL of the above culture medium and sealed with foam plugs filling the necks. A single colony of the desired strain was cultivated overnight (14-16 hrs) in LB medium with appropriate antibiotics and used as the inoculum (1%). After inoculation, flasks were incubated at 37° C. and 200 rpm in an NBS C24 Benchtop Incubator Shaker (New Brunswick Scientific Co., Inc., Edison, N.J.) until an optical density of ~0.3-0.5 was reached, at which point IPTG (5 µM) and cumate (0.1 mM) were added when appropriate. Flasks were then incubated under the same conditions for 48 hrs post-induction.

Figure 7:
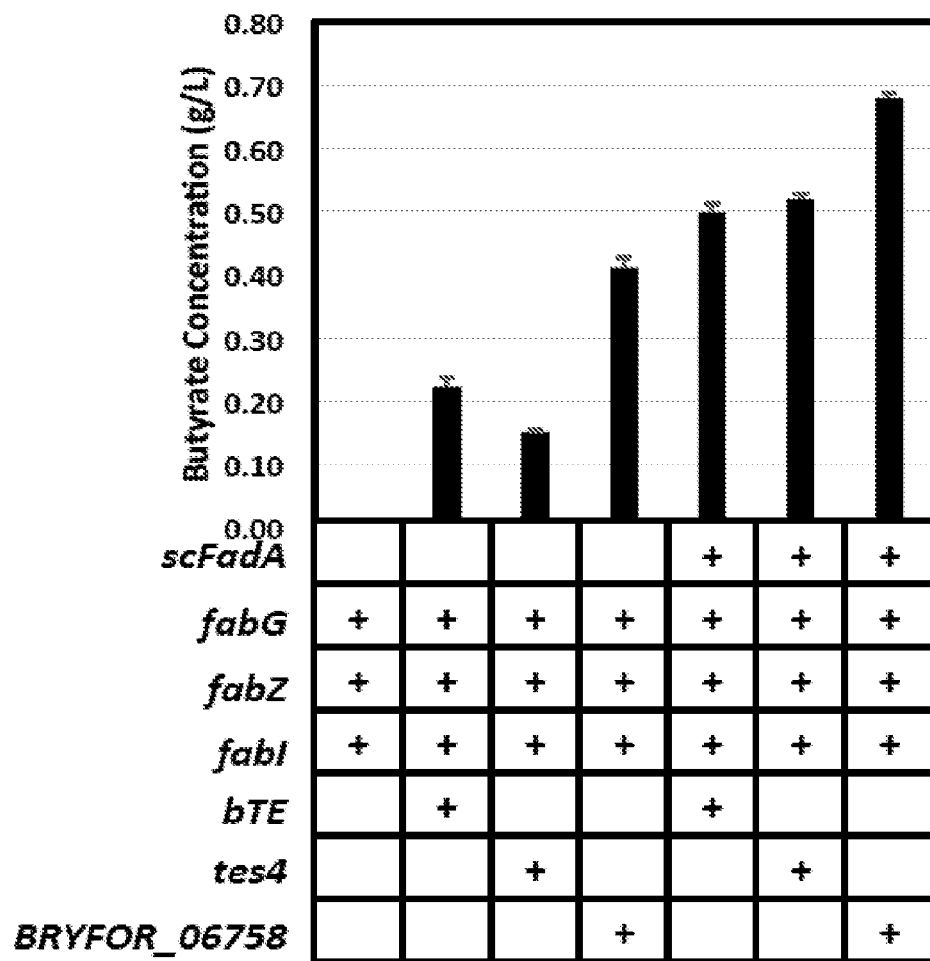
FIG. 7. Modified fatty acid biosynthesis with ACP-dependent thiolase scFadA. Butyrate production shown for the overexpression of ACP-dependent thiolase and acetyl-CoA: ACP transacylase pathway components with fatty acid biosynthesis (FabG, FabZ, FabI) and thioesterase termination enzymes. Data shown for strain JC01(DE3) with indicated overexpressions (+). fabG, fabZ, and fabI overexpressed from pETDuet; bTE, tes4, and BRYFOR_06758 overexpressed from pCDFDuet vector; scFadA expression through cumate controlled chromosomal construct at atoB locus. Strains with scFadA expression also included fadB and fadJ deletions (both involved in beta oxidation).
Figure 8A:
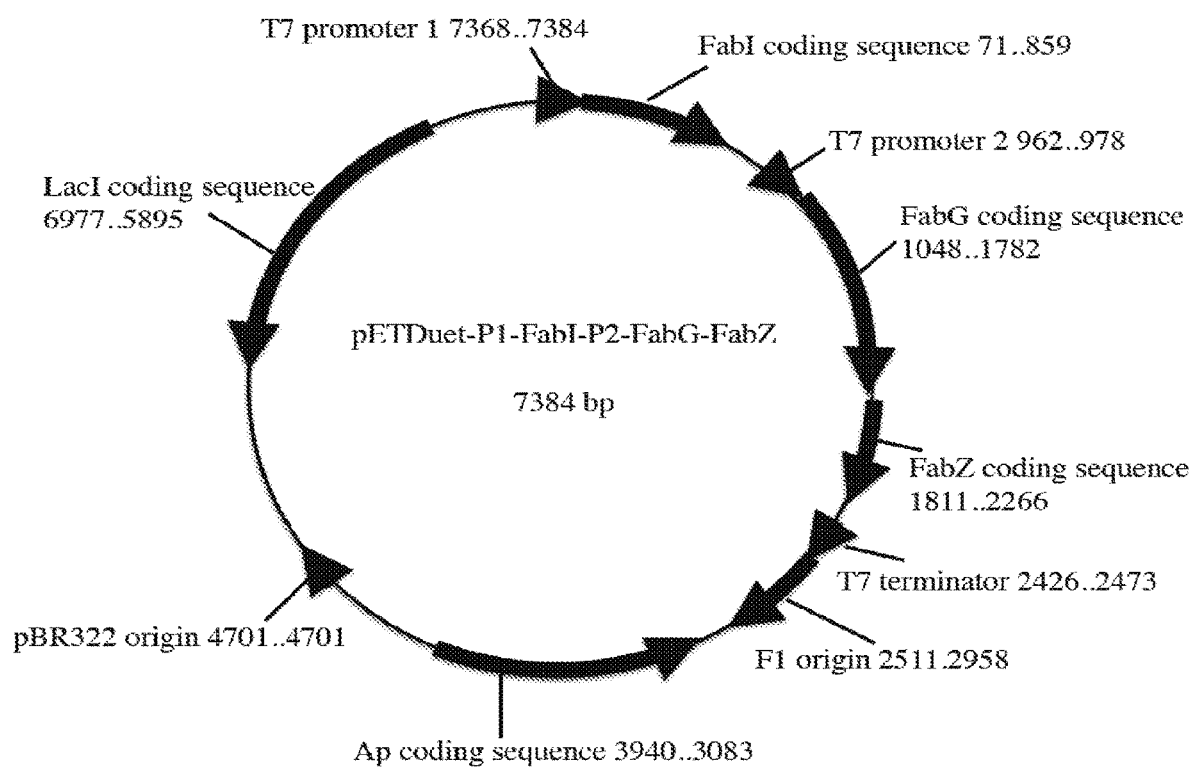
FIG. 8A-D. Plasmid maps of 8A pETDuet-1-P1-FabI-P2-FabG-FabZ; 8B pCDFDuet-P1-P2-bTE; 8C pCDFDuet-P1-P2-tes4; 8D pCDFDuet-P1-P2-BRYFOR_06758.
Figure 8B:
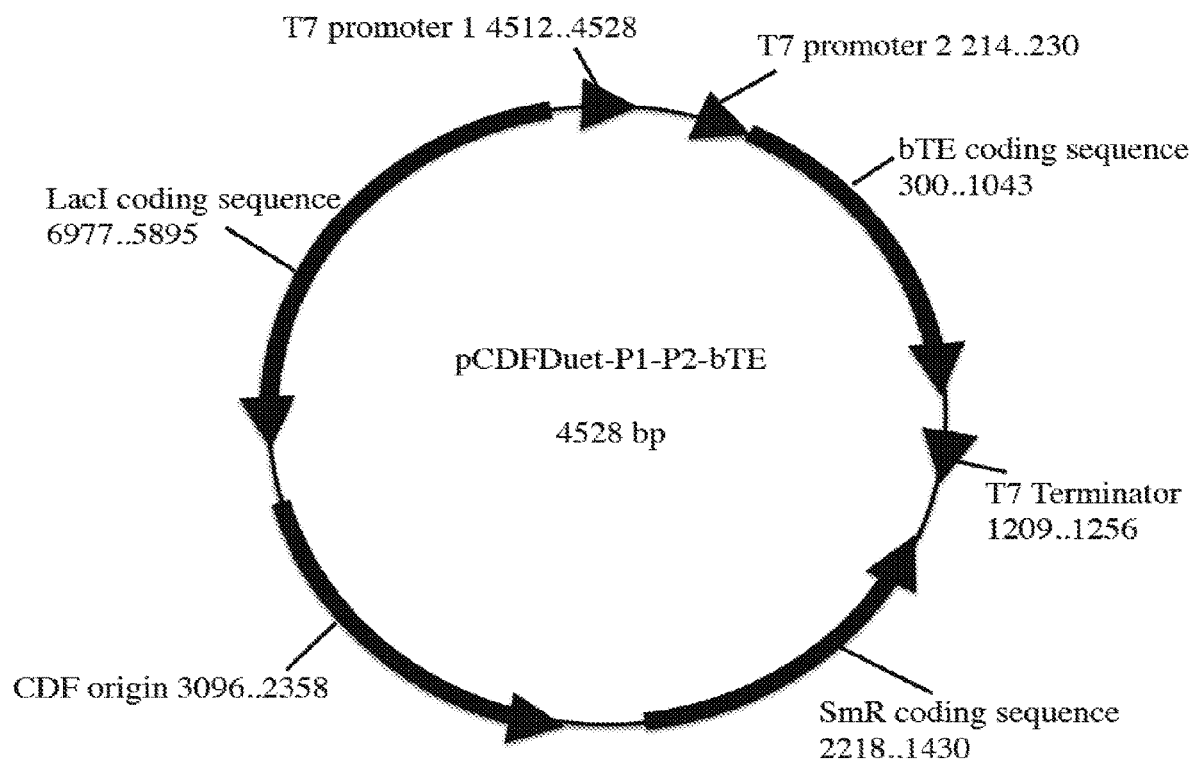
Figure 8C:
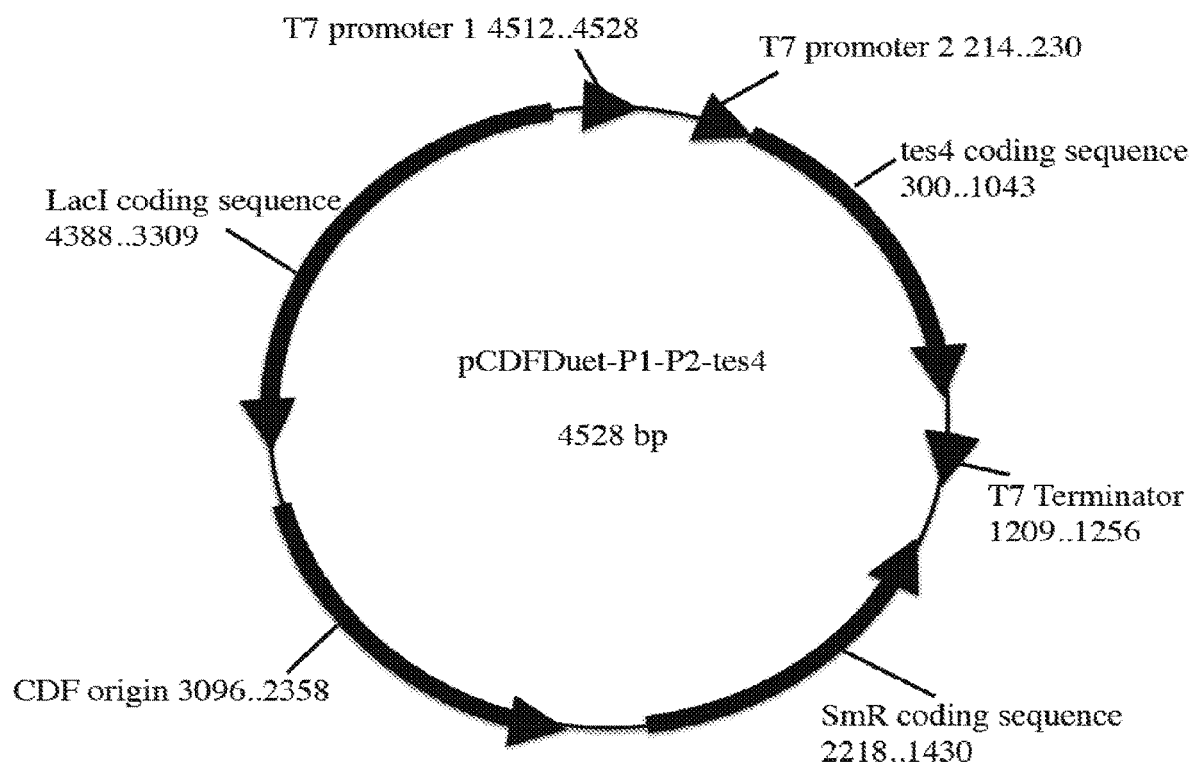
Figure 8D:
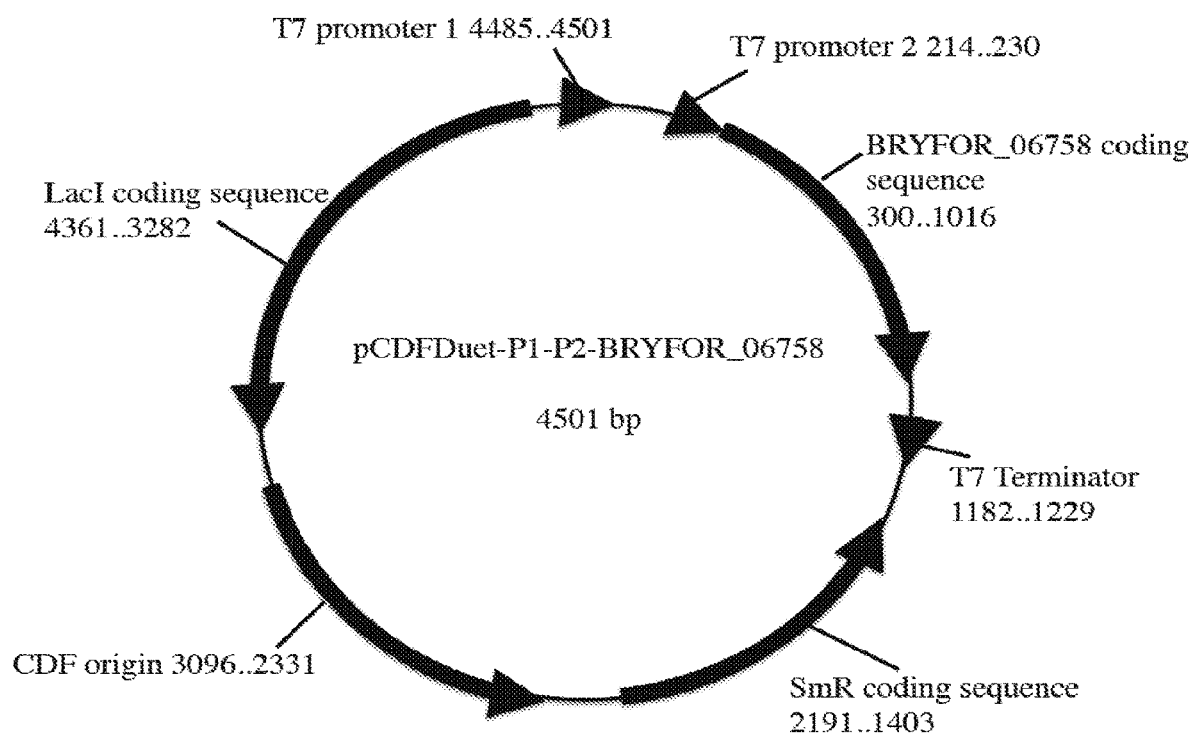

Overexpression of all required pathways components in vivo enabled the synthesis of the 4-carbon carboxylic acid butyrate at levels significantly higher than with fatty acid biosynthesis (FabG, FabZ, FabI) and thioesterase termination alone (FIG. 7), demonstrating the potential for this novel pathway. In fact, the improvement ranges from 30% better, to twice or three times better, depending on which comparisons are made. As such, the use of additional termination pathways functioning with various chain length can be exploited to different chain lengths and types of products as shown in FIGS. 1A-1E.

The above experiments are repeated in Bacillus subtilis. The same genes can be used, especially since Bacillus has no significant codon bias. A protease-deficient strain like WB800N is preferably used for greater stability of heterologous protein. The E. coli-B. subtilis shuttle vector pMTLBS72 exhibiting full structural stability can be used to move the genes easily to a more suitable vector for Bacillus. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available. Since the FAS genes are ubiquitous, the invention is predicted to function in Bacillus.

The above experiments are repeated in yeast. The same genes can be used, but it may be preferred to accommodate codon bias. Several yeast E. coli shuttle vectors are available for ease of the experiments. Since the FAS genes are ubiquitous, the invention is predicted to function in yeast, especially since yeast are already available with exogenous functional TE genes and the reverse beta oxidation pathway has also been made to run in yeast.

Each of the following is incorporated by reference herein in its entirety for all purposes:

U.S. 61/440,192, filed Feb. 7, 2011, WO2013036812, US20130316413 Reverse beta oxidation pathway by Clomburg et al.

U.S. 61/531,911, filed Sep. 7, 2011, WO2013036812 US20140273110 Functionalized carboxylic acids and alcohols by reverse fatty acid oxidation by Gonzalez & Clomburg.

61/932,057, filed Jan. 27, 2014, WO2015112988, Type II fatty acid synthesis enzymes in reverse beta-oxidation by Gonzalez & Clomburg.

All accession numbers (generally in brackets after a gene or protein) are expressly incorporated by reference for all purposes herein. Inclusion of the information at each accession entry, would render the patent of inordinate length, and thus, incorporation of all sequences (and other information found therein) by reference is preferred. A person of ordinary skill in the art will recognize the accession numbers and be able to access them from a variety of databases.

Bergler H, et al., (1996). The Enoyl-[Acyl-Carrier-Protein] Reductase (FabI) of Escherichia coli, which Catalyzes a Key Regulatory Step in Fatty Acid Biosynthesis, Accepts NADH and NADPH as Cofactors and is Inhibited by Palmitoyl-CoA. European Journal of Biochemistry 242(3), 689-94.

Clomburg J M, et al., (2015) Integrated engineering of β-oxidation reversal and ω-oxidation pathways for the synthesis of medium chain ω-functionalized carboxylic acids. Metabolic Engineering 28, 202-12.

Datsenko K A & Wanner B L (2000) One-step inactivation of chromosomal genes in Escherichia coli K-12 using PCR products. PNAS 97(12), 6640-5.

Dellomonaco C, et al., (2011) Engineered reversal of the beta-oxidation cycle for the synthesis of fuels and chemicals. Nature 476, 355-359.

Heath R J & Rock C O. (1996). Roles of the FabA and FabZ β-hydroxyacyl-acyl carrier protein dehydratases in Escherichia coli fatty acid biosynthesis. Journal of Biological Chemistry 271(44), 27795-801.

Jing F, et al., (2011). Phylogenetic and experimental characterization of an acyl-ACP thioesterase family reveals significant diversity in enzymatic specificity and activity. BMC Biochemistry 12(1), 1.

Lobo S, et al., (2001). A Streptomyces collinus thiolase with novel acetyl-CoA: acyl carrier protein transacylase activity. Biochemistry 40(39), 11955-64.

Neidhardt F C, et al., (1974) Culture Medium for Enterobacteria. J Bacteriol 119(3), 736-747.

The invention claimed is:

1. A method of producing a product, comprising growing a genetically engineered microorganism in a culture broth containing glycerol or a sugar, and isolating a product made by a modified fatty acid biosynthesis (FAS) pathway in said microorganism that grows an acyl-ACP primer by adding a 2-carbon donor thereto in each cycle of said FAS pathway, said FAS pathway comprising overexpressing one or more genes encoding:
  a) an acetyl-CoA:ACP transacylase that catalyzes a conversion of acetyl-CoA to an acetyl-ACP primer;
  b) an ACP-dependent thiolase that catalyzes a non-decarboxylative condensation of said acyl-ACP primer with a 2-carbon donor acetyl-ACP or acetyl-CoA to produce a ß-ketoacyl-ACP, said ACP-dependant thiolase selected from E. coli atoB, E. coli yqeF, E. coli fadA, E. coli fadI, Streptomyces collinus fadA, Ralstonia eutropha bktB, Pseudomonas sp. Strain B13 catF, E. coli paaJ, Pseudomonas putida pcaF, Rhodococcus opacus pcaF, Streptomyces sp. pcaF, Ralstonia eutropha phaA, Clostridium acetobutylicum thlA, or Clostridium acetobutylicum thlB;
  c) an 3-oxoacyl-[ACP] reductase that catalyzes a reduction of said ß-ketoacyl-ACP to a ß-hydroxyacyl-ACP;
  d) an 3-hydroxyacyl-[ACP] dehydratase that catalyzes a dehydration of said ß-hydroxyacyl-ACP to a transenoyl-ACP;
  e) an enoyl-[ACP] reductase that catalyzes a reduction of said transenoyl-ACP to an acyl-ACP(+2) that is two carbons longer than said acyl-ACP primer; and,
  f) a termination pathway that catalyzes an exit of an intermediate from steps b-e of said modified FAS pathway to form said product.

2. The method of claim 1, wherein said termination pathway is an ACP cleaving thioesterase, and said microorganism produces a product selected from the group consisting of carboxylic acids, β-hydroxy carboxylic acids, β-keto carboxylic acids, and α,β-unsaturated carboxylic acids.

3. The method of claim 1, wherein said termination pathway is selected from the group consisting of i) an alcohol-forming ACP thioester reductase, and ii) an aldehyde-forming ACP thioester reductase plus an alcohol dehydrogenase, and said microorganism produces a product selected from the group consisting of primary alcohols, 1,-β diols, β-keto primary alcohols, and α,β-unsaturated primary alcohols.

4. The method of claim 1, wherein said termination pathway consists of an aldehyde-forming ACP thioester reductase and an aldehyde decarbonylase, and said microorganism produces a product selected from the group consisting of linear alkanes, linear alkan-3-ols, linear methyl-ketones, and 1-alkenes.

5. The method of claim 1, wherein said termination pathway consists of an aldehyde-forming ACP thioester reductase and a transaminase, and said microorganism produces a product selected from the group consisting of primary amines, β-hydroxyamines, β-keto-amines, and α,β-unsaturated primary amines.

6. The method of claim 2, wherein said microorganism:
a) expresses a carboxylic acid omega hydroxylase and produces a product selected from the group consisting of ω-hydroxylated carboxylic acids, β,ω-dihydroxy carboxylic acids, β-keto-ω-hydroxy carboxylic acids, and α,β-unsaturated ω-hydroxylated carboxylic acids;
b) expresses a carboxylic acid co hydroxylase, an alcohol oxidase, and an aldehyde dehydrogenase, and produces a product selected from the group consisting of di-carboxylic acids, (3R)-β-hydroxy di-carboxylic acids, β-keto di-carboxylic acids, and α,β-unsaturated di-carboxylic acids; or
c) expresses a carboxylic acid alpha hydroxylase, and produces a product selected from the group alpha-hydroxy carboxylic acids, α,β-dihydroxy carboxylic acids, α-hydroxy, β-keto carboxylic acids, and α,β-unsaturated α-hydroxy carboxylic acids.

7. The method of claim 3, wherein said microorganism:
a) expresses a carboxylic acid co hydroxylase, an alcohol oxidase, and an aldehyde dehydrogenase, and produces a product selected from the group consisting of ω-hydroxylated carboxylic acids, β,ω-dihydroxy carboxylic acids, β-keto-ω-hydroxy carboxylic acids, and α,β-unsaturated omega-hydroxylated carboxylic acids;
b) expresses a carboxylic acid co hydroxylase, and produces a product selected from the group consisting of 1,ω-diols, 1,β,ω-triols, β-keto-1,ω-diols, and α,β-unsaturated 1,ω-diols;
c) expresses a carboxylic acid ω hydroxylase, an alcohol oxidase, and a transaminase, and produces a product selected from the group consisting of primary alkanolamines, ω-hydroxyamines, β-hydroxy primary alkanolamines, β-keto primary alkanolamines, and α,β-unsaturated primary alkanolamines; or
d) expresses a carboxylic acid and a hydroxylase, and produces a product selected from the group consisting of 1,2-diols, 1,2,3-triols, β-keto, 1,2-diols, and α,β-unsaturated 1,2-diols.

8. The method of claim 5, wherein said microorganism:
a) expresses a carboxylic acid ω hydroxylase, and produces a product selected from the group consisting of primary alkanolamines, ω-hydroxyamines, β-hydroxy primary alkanolamines, β-keto primary alkanolamines, and α,β-unsaturated primary alkanolamines;
b) expresses a carboxylic acid ω hydroxylase, an alcohol oxidase, and an aldehyde dehydrogenase, and produces a product selected from the group consisting of ω-amino acids, β-hydroxy-ω-amino acids, β-keto-ω-amino acids, and α,β-unsaturated ω-amino acids; or
c) expresses a carboxylic acid and a hydroxylase, and produces a product selected from the group consisting of α-hydroxylated primary amines, α,β-dihydroxy primary amines, α-hydroxy-β-keto primary amines, and α-hydroxy-α,β-unsaturated primary amines.

9. The method of claim 1, said microorganism further comprising reduced expression of genes leading to reduced production of lactate, acetate, ethanol and succinate.

10. The method of claim 1, wherein said overexpressed acetyl-CoA:ACP transacylase is encoded by *E. coli* fabD or *Streptomyces collinus* fadA.

11. The method of claim 1, wherein:
a) said overexpressed 3-oxoacyl-[ACP] reductase is encoded by *E. coli* fabG;
b) said overexpressed 3-hydroxyacyl-[ACP] dehydratase is encoded by *E. coli* fabA, or *E. coli* fabZ; and
c) said enoyl-[ACP] reductase is encoded by *E. coli* fabI, *Enterococcus faecalis* fabK, *Bacillus subtilis* fabL, or *Vibrio cholerae* fabV.

12. The method of claim 2, wherein said overexpressed ACP-cleaving thioesterase is encoded by *E. coli* tesA, *Cuphea palustris* fatB1, *Cuphea viscosissima* fatB3, *Ulmus americana* fatB1, *Cocos nucifera* fatB2, *Elaeis guineensis* PTE, *Clostridium perfringens* CPF 2954, *Umbellularia californica* fatB1, *Bacteroides thetaiotaomicron* bTE, *Bacteroides fragilis* tes4, or *Marvinbryantia formatexigens* BRY-FOR_06758.

13. The method of claim 3, wherein:
a) said overexpressed alcohol-forming ACP thioester reductase is encoded by *Marinobacter aquaeolei* VT8 maqu 2220, *Hahella chejuensis* hch_05075, *Marinobacter algicola* MDG893_11561, or *Bermanella marisrubri* RED65_09894;
b) said overexpressed aldehyde-forming ACP thioester reductase is encoded by *Nostoc punctiforme* Npun_R1710, *Synechococcus elongates* Synpcc7942_1594, *Prochlorococcus marinus* P9515_05971, or *Synechocystis* sp. PCC 6803 s110209; or
c) said overexpressed alcohol dehydrogenase is encoded by *E. coli* beta, *E. coli* dkgA, *E. coli* eutG, *E. coli* fucO, *E. coli* ucpA, *E. coli* yahK, *E. coli* ybbO, *E. coli* ybdH, *E. coli* yiaY, or *E. coli* yjgB.

14. The method of claim 4, wherein said overexpressed aldehyde-forming ACP thioester reductase is encoded by *Nostoc punctiforme* Npun_R1710, *Synechococcus elongates* Synpcc7942_1594, *Prochlorococcus marinus* P9515_05971, or *Synechocystis* sp. PCC 6803 s110209 and wherein said overexpressed aldehyde decarbonylase is encoded by *Synechococcus elongates* PCC7942 orf1593, *Nostoc punctiforme* PCC73102 npun_R1711, or *Prochlorococcus marinus* MIT9313 pmt1231.

15. The method of claim 5, wherein said overexpressed transaminase is encoded by *Arabidopsis thaliana* At3g22200, *Alcaligenes denitrificans* aptA, *Bordetella bronchiseptica* BB0869, *Bordetella parapertussis* BPP0784, *Brucella melitensis* BAWG 0478, *Burkholderia pseudomallei* BP1026B_I0669, *Chromobacterium violaceum* CV2025, *Oceanicola granulosus* OG2516_07293, *Paracoccus denitrificans* PD1222 Pden_3984, *Pseudogulbenkiania ferrooxidans* ω-TA, *Pseudomonas putida* ω-TA, *Ralstonia solanacearum* ω-TA, *Rhizobium meliloti* SMc01534, *Vibrio fluvialis* ω-TA, *Mus musculus* abaT, or *E. coli* gabT.

16. The method of claim 6, wherein said overexpressed carboxylic acid omega hydroxylase is encoded by

*Pseudomonas putida* alkBGT, *Marinobacter aquaeolei* CYP153A, *Mycobacterium marinum* CYP153A16, *Polaromonas* sp. CYP153A, *Nicotiana tabacum* CYP94A5, *Vicia sativa* CYP94A1, *Vicia sativa* CYP94A2, *Arabidopsis thaliana* CYP94B1, *Arabidopsis thaliana* CYP86A8, *Candida tropicalis, Candida tropicalis* CYP52A2, or *Homo sapiens* CYP4A11.

17. The method of claim 7, wherein:
a) said overexpressed alcohol oxidase is encoded by *Rhodococcus ruber* SC1 cddC, *Acinetobacter* sp. SE19 chnD, *E. coli* yahK, or *E. coli* yjgB;
b) said overexpressed aldehyde dehydrogenase is encoded by *Rhodococcus ruber* SC1 cddD, or *Acinetobacter* sp. SE19 chnE, or c) said overexpressed fatty acid alpha hydroxylases is encoded by *Myxococcus xanthus* MXAN_0191, or *Stigmatella aurantiaca* STIAU_3334.

18. The method of claim 1, wherein:
a) said ACP-dependent thiolase is an engineered variant of enzymes encoded by *E. coli* atoB, *E. coli* yqeF, *E. coli* fadA, *E. coli* faII, *Streptomyces collinus* fadA, *Ralstonia eutropha* bktB, *Pseudomonas* sp. Strain B13 catF, *E. coli* paaJ, *Pseudomonas putida* pcaF, *Rhodococcus opacus* pcaF, *Streptomyces* sp. pcaF, *Ralstonia eutropha* phaA, *Clostridium acetobutylicum* thlA, or *Clostridium acetobutylicum* th1B, and is able to catalyze the non-decarboxylative condensation of an omega-hydroxylated primer, an omega-carboxylated primer, an omega-phenyl-terminated primer, an omega-aminated primer, or an aliphatic branched primer with acetyl-ACP;
b) said overexpressed 3-oxoacyl-[ACP] reductase, overexpressed 3-hydroxyacyl-[ACP] dehydratase, and overexpressed enoyl-[ACP] reductase are able to act on omega-hydroxylated, omega-carboxylated, omega-phenyl-terminated, omega-aminated, or aliphatic branched substrates and encoded by genes selected from the group consisting of *E. coli* fabG, *E. coli* fabA, *E. coli* fabZ, *E. coli* fabI, *Enterococcus faecalis* fabK, *Bacillus subtilis* fabL and *Vibrio cholerae* fabV; and
c) said overexpressed termination pathway is able to act on omega-hydroxylated, omega-carboxylated or omega-aminated substrates and encoded by genes selected from the group consisting of *E. coli* tesA, *Cuphea palustris* fatB1, *Cuphea viscosissima* fatB3, *Ulmus americana* fatB1, *Cocos nucifera* fatB2, *Elaeis guineensis* PTE, *Clostridium perfringens* CPF 2954, *Umbellularia californica* fatB1, *Marinobacter aquaeolei* VT8 maqu 2220, *Hahella chejuensis* hch_05075, *Marinobacter algicola* MDG893_11561, *Bermanella marisrubri* RED65_09894, *Nostoc punctiforme* Npun_R1710, *Synechococcus elongates* Synpcc7942_1594, *Prochlorococcus marinus* P9515_05971, *Synechocystis* sp. PCC 6803 sll0209, *E. coli* beta, *E. coli* dkgA, *E. coli* eutG, *E. coli* fucO, *E. coli* ucpA, *E. coli* yahK, *E. coli* ybbO, *E. coli* ybdH, *E. coli* yiaY, *E. coli* yjgB, *Synechococcus elongates* PCC7942 orf1593, *Nostoc punctiforme* PCC73102 npun_R1711, *Prochlorococcus marinus* MIT9313 pmt1231, *Arabidopsis thaliana* At3g22200, *Alcaligenes denitrificans* aptA, *Bordetella bronchiseptica* BB0869, *Bordetella parapertussis* BPP0784, *Brucella melitensis* BAWG_0478, *Burkholderia pseudomallei* BP1026B_I0669, *Chromobacterium violaceum* CV2025, *Oceanicola granulosus* OG2516_07293, *Paracoccus denitrificans* PD1222 Pden_3984, *Pseudogulbenkiania ferrooxidans* ω-TA, *Pseudomonas putida* ω-TA, *Ralstonia solanacearum* ω-TA, *Rhizobium meliloti* SMc01534, *Vibrio fluvialis* ω-TA, *Mus musculus* abaT, and *E. coli* gabT.

19. The method of claim 1, further comprising ΔadhE; Δpta or ΔackA or ΔackApta; ΔpoxB; ΔldhA; and ΔfrdA and producing less acetate, lactate, ethanol and succinate.

* * * * *

UNITED STATES PATENT AND TRADEMARK OFFICE
CERTIFICATE OF CORRECTION

PATENT NO.        : 11,319,562 B2
APPLICATION NO.   : 16/815790
DATED             : May 3, 2022
INVENTOR(S)       : Gonzalez et al.

It is certified that error appears in the above-identified patent and that said Letters Patent is hereby corrected as shown below:

In the Claims

On Column 29, Line 27, of Claim 6 b):
'expresses a carboxylic acid co hydroxylase, an alcohol'
Should read as:
---expresses a carboxylic acid ω hydroxylase, an alcohol---

On Column 29, Line 39, of Claim 7 a):
'expresses a carboxylic acid co hydroxylase, an alcohol'
Should read as:
---expresses a carboxylic acid ω hydroxylase, an alcohol---

On Column 29, Line 45, of Claim 7 b):
'expresses a carboxylic acid co hydroxylase, an alcohol'
Should read as:
---expresses a carboxylic acid ω hydroxylase, and pro- ---

On Column 31, Line 21, Claim 18 a):
'coli fadA, E. coli fall, streptomyces collinus fadA,'
Should read as:
---coli fadA, E. coli fadl, streptomyces collinus fadA,---

Signed and Sealed this
Fourth Day of October, 2022

Katherine Kelly Vidal
*Director of the United States Patent and Trademark Office*